US009110082B2

(12) United States Patent
Sathyanarayanan et al.

(10) Patent No.: US 9,110,082 B2
(45) Date of Patent: Aug. 18, 2015

(54) METHODS FOR THE IDENTIFICATION AND TREATMENT OF PATIENTS SENSITIVE TO ANTI IGF-1R INHIBITION THERAPY

(75) Inventors: Sriram Sathyanarayanan, Natick, MA (US); Christopher Winter, Swampscott, MA (US); Youyuan Xu, Needham, MA (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 171 days.

(21) Appl. No.: 13/512,061

(22) PCT Filed: Nov. 22, 2010

(86) PCT No.: PCT/US2010/057552
§ 371 (c)(1),
(2), (4) Date: Oct. 2, 2012

(87) PCT Pub. No.: WO2011/066200
PCT Pub. Date: Jun. 3, 2011

(65) Prior Publication Data
US 2013/0323232 A1    Dec. 5, 2013

Related U.S. Application Data

(60) Provisional application No. 61/264,958, filed on Nov. 30, 2009.

(51) Int. Cl.
| | |
|---|---|
| *G01N 33/68* | (2006.01) |
| *A61N 5/02* | (2006.01) |
| *A61N 5/10* | (2006.01) |
| *C12Q 1/68* | (2006.01) |
| *G01N 33/50* | (2006.01) |
| *A61K 39/395* | (2006.01) |
| *A61K 45/06* | (2006.01) |
| *A61N 5/06* | (2006.01) |

(52) U.S. Cl.
CPC ...... *G01N 33/6893* (2013.01); *A61K 39/39558* (2013.01); *A61K 45/06* (2013.01); *A61N 5/02* (2013.01); *A61N 5/06* (2013.01); *A61N 5/10* (2013.01); *C12Q 1/6886* (2013.01); *G01N 33/5044* (2013.01); *G01N 33/5091* (2013.01); *C12Q 2600/106* (2013.01); *C12Q 2600/112* (2013.01); *C12Q 2600/136* (2013.01); *G01N 2333/475* (2013.01)

(58) Field of Classification Search
None
See application file for complete search history.

(56) References Cited

U.S. PATENT DOCUMENTS

| 6,337,338 B1 * | 1/2002 | Kozlowski et al. ........... 514/311 |
| 2005/0084906 A1 | 4/2005 | Goetsch et al. |
| 2009/0285824 A1 | 11/2009 | Calzone et al. |

FOREIGN PATENT DOCUMENTS

| WO | WO03/059951 | 7/2003 |
| WO | WO2008/144345 | 11/2008 |
| WO | WO2009/079587 | 6/2009 |
| WO | WO2009/102986 | 8/2009 |

OTHER PUBLICATIONS

Contreras CM, Gurumurthy S, Haynie JM, Shirley LJ, Akbay EA, Wingo SN, Schorge JO, Broaddus RR, Wong KK, Bardeesy N, Castrillon DH. Loss of Lkb1 provokes highly invasive endometrial adenocarcinomas. Cancer Res. Feb. 1, 2008;68(3):759-66.
Sanchez-Cespedes M, Parrella P, Esteller M, Nomoto S, Trink B, Engles JM, Westra WH, Herman JG, Sidransky D. Inactivation of LKB1/STK11 is a common event in adenocarcinomas of the lung. Cancer Res. Jul. 1, 2002;62(13):3659-62.
Ji H, Ramsey MR, Hayes DN, Fan C, McNamara K, Kozlowski P, Torrice C, Wu MC, Shimamura T, Perera SA, Liang MC, Cai D, Naumov GN, Bao L, Contreras CM, Li D, Chen L, Krishnamurthy J, Koivunen J, Chirieac LR, Padera RF, Bronson RT, Lindeman NI, Christiani DC, Lin X, Shapiro GI, Jänne PA, Johnson BE, Meyerson M, Kwiatkowski DJ, Castrillon DH, Bardeesy N, Sharpless NE, Wong KK. LKB1 modulates lung cancer differentiation and metastasis. Nature. Aug. 16, 2007;448(7155):807-10. Epub Aug. 5, 2007.
Wingo SN, Gallardo TD, Akbay EA, Liang MC, Contreras CM, Boren T, Shimamura T, Miller DS, Sharpless NE, Bardeesy N, Kwiatkowski DJ, Schorge JO, Wong KK, Castrillon DH. Somatic LKB1 mutations promote cervical cancer progression. PLoS One. 2009;4(4):e5137. Epub Apr. 2, 2009.
Shaw RJ. Tumor suppression by LKB1: SIK-ness prevents metastasis. Sci Signal. Sep. 1, 2009;2(86):pe55.
Young RH. Sex cord-stromal tumors of the ovary and testis: their similarities and differences with consideration of selected problems. Mod Pathol. Feb. 2005;18 Suppl 2:S81-98.
Esteller M, Avizienyte E, Corn PG, Lothe RA, Baylin SB, Aaltonen LA, Herman JG. Epigenetic inactivation of LKB1 in primary tumors associated with the Peutz-Jeghers syndrome. Oncogene. Jan. 6, 2000;19(1):164-8.
Hemminki A, Markle D, Tomlinson I, Avizienyte E, Roth S, Loukola A, Bignell G, Warren W, Aminoff M, Höglund P, Järvinen H, Kristo P, Pelin K, Ridanpää M, Salovaara R, Toro T, Bodmer W, Olschwang S, Olsen AS, Stratton MR, de la Chapelle A, Aaltonen LA. A serine/threonine kinase gene defective in Peutz-Jeghers syndrome. Nature. Jan. 8, 1998;391(6663):184-7.
Westerman AM, Entius MM, de Baar E, Boor PP, Koole R, van Velthuysen ML, Offerhaus GJ, Lindhout D, de Rooij FW, Wilson JH. Peutz-Jeghers syndrome: 78-year follow-up of the original family. Lancet. Apr. 10, 1999;353(9160):1211-5.
Sanchez-Cespedes M. A role for LKB1 gene in human cancer beyond the Peutz-Jeghers syndrome. Oncogene. Dec. 13, 2007;26(57):7825-32. Epub Jun. 18, 2007.

(Continued)

*Primary Examiner* — Brian J Gangle
*Assistant Examiner* — Andrea McCollum

(57) ABSTRACT

The present invention relates to methods for treating a dalotuzumab responsive cancer, in a patient, comprising determining the expression level of liver kinase B1 (LKB1), in a cancer cell from the patient, and when said expression is determined to be lower than that of a control cell; administering, to said patient, a therapeutically effective amount of dalotuzumab. The invention also relates to methods for assessing neoplastic cells, selecting patients, selecting therapies as well as diagnostic methods.

12 Claims, 6 Drawing Sheets

(56) References Cited

OTHER PUBLICATIONS

Hemminki A. The molecular basis and clinical aspects of Peutz-Jeghers syndrome. Cell Mol Life Sci. May 1999;55(5):735-50.

Giardiello FM, Welsh SB, Hamilton SR, Offerhaus GJ, Gittelsohn AM, Booker SV, Krush AJ, Yardley JH, Luk GD. Increased risk of cancer in the Peutz-Jeghers syndrome. N Engl J Med. Jun. 11, 1987;316(24):1511-4.

Amin RM, Hiroshima K, Iyoda A, Hoshi K, Honma K, Kuroki M, Kokubo T, Fujisawa T, Miyagi Y, Nakatani Y. LKB1 protein expression in neuroendocrine tumors of the lung. Pathol Int. Feb. 2008;58(2):84-8.

Zhao JJ, Gjoerup OV, Subramanian RR, Cheng Y, Chen W, Roberts TM, Hahn WC. Human mammary epithelial cell transformation through the activation of phosphatidylinositol 3-kinase. Cancer Cell. May 2003;3(5):483-95.

Yin M, Guan X, Liao Z, Wei Q. Insulin-like growth factor-1 receptor-targeted therapy for non-small cell lung cancer: a mini review. Am J Transl Res. Jan. 30, 2009;1(2):101-14.

Shackelford DB, Shaw RJ. The LKB1-AMPK pathway: metabolism and growth control in tumour suppression. Nat Rev Cancer. Aug. 2009;9(8):563-75.

Fan D, Ma C, Zhang H. The molecular mechanisms that underlie the tumor suppressor function of LKB1. Acta Biochim Biophys Sin (Shanghai) Feb. 2009;41(2):97-107.

Hezel AF, Bardeesy N. LKB1; linking cell structure and tumor suppression. Oncogene. Nov. 24, 2008;27(55):6908-19.

Volikos E, Robinson J, Aittomäki K, Mecklin JP, Järvinen H, Westerman AM, de Rooij FW, Vogel T, Moeslein G, Launonen V, Tomlinson IP, Silver AR, Aaltonen LA. LKB1 exonic and whole gene deletions are a common cause of Peutz-Jeghers syndrome. J Med Genet. May 2006;43(5):e18.

Alessi DR, Sakamoto K, Bayascas JR. LKB1-dependent signaling pathways. Annu Rev Biochem. 2006;75:137-63.

Launonen V. Mutations in the human LKB1/STK11 gene. Hum Mutat. Oct. 2005;26(4):291-7.

Greenbaum et al., Interrelating different types of genomic data, from proteome to secretome: 'oming in on function. Genome Research, vol. 11, No. 9, pp 1463-1468, 2001.

Yarden Y, et al., CTEN and LKB1: novel tumor biomarkers for breast cancer implications of resistance and response to tyrosine kinase inhibitor (TKI)-based therapies in breast cancer. Breast Cancer Research, vol. 106, No. Suppl. 1, p. S159, 2007.

Burzawa, J. et al., Preclinical evidence for exercise and pharmacologic exercise mimetics in the treatment of endometrial cancer. Gynecologic Oncology, vol. 116, No. 3, pp. S80-S81, 2010.

He TY, Tsai LH, Huang CC, Chou MC, Lee H. LKB1 Loss at Transcriptional Level Promotes Tumor Malignancy and Poor Patient Outcomes in Colorectal Cancer. Ann Surg Oncol. May 31, 2014. [Epub ahead of print].

* cited by examiner

SEQUENCE LISTING

<160> NUMBER OF SEQ ID NOS: 16

<210> SEQ ID NO 1
<211> LENGTH: 433
<212> TYPE: PRT
<213> ORGANISM: Homo sapiens

<400> SEQUENCE: 1

```
Met Glu Val Val Asp Pro Gln Gln Leu Gly Met Phe Thr Glu Gly Glu
1               5                   10                  15

Leu Met Ser Val Gly Met Asp Thr Phe Ile His Arg Ile Asp Ser Thr
            20                  25                  30

Glu Val Ile Tyr Gln Pro Arg Arg Lys Arg Ala Lys Leu Ile Gly Lys
        35                  40                  45

Tyr Leu Met Gly Asp Leu Leu Gly Glu Gly Ser Tyr Gly Lys Val Lys
    50                  55                  60

Glu Val Leu Asp Ser Glu Thr Leu Cys Arg Arg Ala Val Lys Ile Leu
65                  70                  75                  80

Lys Lys Lys Lys Leu Arg Arg Ile Pro Asn Gly Glu Ala Asn Val Lys
                85                  90                  95

Lys Glu Ile Gln Leu Leu Arg Arg Leu Arg His Lys Asn Val Ile Gln
            100                 105                 110

Leu Val Asp Val Leu Tyr Asn Glu Glu Lys Gln Lys Met Tyr Met Val
        115                 120                 125

Met Glu Tyr Cys Val Cys Gly Met Gln Glu Met Leu Asp Ser Val Pro
    130                 135                 140

Glu Lys Arg Phe Pro Val Cys Gln Ala His Gly Tyr Phe Cys Gln Leu
145                 150                 155                 160

Ile Asp Gly Leu Glu Tyr Leu His Ser Gln Gly Ile Val His Lys Asp
                165                 170                 175

Ile Lys Pro Gly Asn Leu Leu Leu Thr Thr Gly Gly Thr Leu Lys Ile
            180                 185                 190

Ser Asp Leu Gly Val Ala Glu Ala Leu His Pro Phe Ala Ala Asp Asp
        195                 200                 205
```

```
Thr Cys Arg Thr Ser Gln Gly Ser Pro Ala Phe Gln Pro Pro Glu Ile
210                 215                 220

Ala Asn Gly Leu Asp Thr Phe Ser Gly Phe Lys Val Asp Ile Trp Ser
225                 230                 235                 240

Ala Gly Val Thr Leu Tyr Asn Ile Thr Thr Gly Leu Tyr Pro Phe Glu
            245                 250                 255

Gly Asp Asn Ile Tyr Lys Leu Phe Glu Asn Ile Gly Lys Gly Ser Tyr
            260                 265                 270

Ala Ile Pro Gly Asp Cys Gly Pro Pro Leu Ser Asp Leu Leu Lys Gly
            275                 280                 285

Met Leu Glu Tyr Glu Pro Ala Lys Arg Phe Ser Ile Arg Gln Ile Arg
290                 295                 300

Gln His Ser Trp Phe Arg Lys Lys His Pro Ala Glu Ala Pro Val
305                 310                 315                 320

Pro Ile Pro Pro Ser Pro Asp Thr Lys Asp Arg Trp Arg Ser Met Thr
                325                 330                 335

Val Val Pro Tyr Leu Glu Asp Leu His Gly Ala Asp Glu Asp Glu Asp
            340                 345                 350

Leu Phe Asp Ile Glu Asp Asp Ile Ile Tyr Thr Gln Asp Phe Thr Val
            355                 360                 365

Pro Gly Gln Val Pro Glu Glu Glu Ala Ser His Asn Gly Gln Arg Arg
370                 375                 380

Gly Leu Pro Lys Ala Val Cys Met Asn Gly Thr Glu Ala Ala Gln Leu
385                 390                 395                 400

Ser Thr Lys Ser Arg Ala Glu Gly Arg Ala Pro Asn Pro Ala Arg Lys
                405                 410                 415

Ala Cys Ser Ala Ser Ser Lys Ile Arg Arg Leu Ser Ala Cys Lys Gln
                420                 425                 430

Gln
```

<210> SEQ ID NO 2
<211> LENGTH: 3285
<212> TYPE: DNA
<213> ORGANISM: Homo sapiens

<400> SEQUENCE: 2

```
gcgtgtcggg cgcggaaggg ggaggcggcc cggggcgccc gcgagtgagg cgcggggcgg    60
cgaagggagc gcgggtggcg gcacttgctg ccgcggcctt ggatgggctg ggccccctc   120
gccgctccgc ctcctccaca cgcgcggcgg ccgcggcgag ggggacgcgc cgcccggggc   180
ccggcacctt cgggaacccc ccggcccgga gcctgcggcc tgcgccgcct cggccgccgg   240
gagccccgtg gagcccccgc cgccgcgccg ccccgcggac cggacgctga gggcactcgg   300
ggcggggcgc gcgctcgggc agacgtttgc ggggagggg gcgcctgccg ggccccggcg   360
accaccttgg gggtcgcggg ccggctcggg gggcgcccag tgcgggccct cgcgggcgcc   420
gggcagcgac cagccctgag cggagctgtt ggccgcggcg ggaggcctcc cggacgcccc   480
cagccccccg aacgctcgcc cgggccggcg ggagtcggcg ccccccggga ggtccgctcg   540
gtcgtccgcg gcggagcgtt tgctcctggg acaggcggtg ggaccgggc gtcgccggag   600
acgcccccag cgaagttggg ctctccaggt gtggggtcc cggggggtag cgacgtcgcg   660
gacccggcct gtgggatggg cggcccggag aagactgcgc tcggccgtgt tcatacttgt   720
ccgtgggcct gaggtccccg gaggatgacc tagcactgaa aagccccggc cggcctcccc   780
agggtccccg aggacgaagt tgaccctgac cgggccgtct cccagttctg aggcccgggt   840
```

```
cccactggaa ctcgcgtctg agccgccgtc ccggaccccc ggtgcccgcc ggtccgcaga    900
ccctgcaccg ggcttggact cgcagccggg actgacgtgt agaacaatcg tttctgttgg    960
aagaagggtt tttcccttcc ttttgggtt tttgttgcct ttttttttc ttttttcttt     1020
gtaaattt ggagaaggga agtcggaaca caaggaagga ccgctcaccc gcggactcag     1080
ggctggcggc gggactccag gaccctgggt ccagcatgga ggtggtggac ccgcagcagc    1140
tgggcatgtt cacggagggc gagctgatgt cggtgggtat ggacacgttc atccaccgca    1200
tcgactccac cgaggtcatc taccagccgc ccgcaagcg ggccaagctc atcggcaagt    1260
acctgatggg ggacctgctg ggggaaggct cttacggcaa ggtgaaggag gtgctggact    1320
cggagacgct gtgcaggagg gccgtcaaga tcctcaagaa gaagaagttg cgaaggatcc    1380
ccaacgggga ggccaacgtg aagaaggaaa ttcaactact gaggaggtta cggcacaaaa    1440
atgtcatcca gctggtggat gtgttataca acgaagagaa gcagaaaatg tatatggtga    1500
tggagtactg cgtgtgtggc atgcaggaaa tgctggacag cgtgccggag aagcgtttcc    1560
cagtgtgcca ggcccacggg tacttctgtc agctgattga cggcctggag tacctgcata    1620
gccagggcat tgtgcacaag gacatcaagc cggggaacct gctgctcacc accggtggca    1680
ccctcaaaat ctccgacctg ggcgtggccg aggcactgca cccgttcgcg gcggacgaca    1740
cctgccggac cagccagggc tccccggctt ccagccgcc cgagattgcc aacgcctgg     1800
acaccttctc cggcttcaag gtggacatct ggtcggctgg ggtcacctc tacaacatca    1860
ccacgggtct gtaccccttc gaagggaca acatctacaa gttgtttgag aacatcggga    1920
aggggagcta cgccatcccg ggcgactgtg cccccgct ctctgacctg ctgaaaggga    1980
tgcttgagta cgaaccggcc aagaggttct ccatccggca gatccggcag cacagctggt    2040
tccggaagaa acatcctccg gctgaagcac cagtgcccat cccaccgagc ccagacacca    2100
aggaccggtg cgcagcatg actgtggtgc cgtacttgga ggacctgcac ggcgcggacg    2160
aggacgagga cctcttcgac atcgaggatg acatcatcta cactcaggac ttcacggtgc    2220
ccggacaggt cccagaagag gaggccagtc acaatggaca cgccggggc ctccccaagg    2280
ccgtgtgtat gaacggcaca gaggcggcgc agctgagcac caaatccagg gcggagggcc    2340
gggccccaa ccctgccgc aaggcctgct ccgccagcag caagatccgc cggctgtcgg    2400
cctgcaagca gcagtgaggc tggccgcctg cagcccgtgt ccaggagccc cgccaggtgc    2460
ccgcgccagg ccctcagtct tcctgccggt tccgcccgcc ctccggaga ggtggccgcc    2520
atgcttctgt gccgaccacg ccccaggacc tccgagcgc cctgcagggc cgggcagggg    2580
gacagcaggg accggcgca gccctccccc ctcggccgcc cggcagtgca cgcggcttgt    2640
tgacttcgca gccccgggcg gagccttccc gggcgggcgt gggaggaggg aggcggcctc    2700
catgcacttt atgtggagac tactggcccc gccgtggcc tcgtgctccg cagggcgccc    2760
agcgccgtcc ggcggccccg ccgcagacca gctggcgggt gtggagacca ggctcctgac    2820
cccgccatgc atgcagcgcc acctggaagc gcgcggccg ctttggtttt tgtttggtt    2880
ggttccattt tctttttttc tttttttttt taagaaaaaa taaaaggtgg atttgagctg    2940
ggctgtgagg ggtgtttggg agctgctggg tggcaggggg gctgtggggt cgggctcacg    3000
tcgcggccgc ctttgcgctc tcgggtcacc ctgctttggc ggcccggccg gagggcagga    3060
ccctcacctc tccccaagg ccactgcgct cttgggaccc cagagaaaac ccggagcaag    3120
caggagtgtg cggtcaatat ttatatcatc cagaaaagaa aaacacgaga aacgccatcg    3180
```

```
cgggatggtg cagacgcggc ggggactcgg agggtgccgt gcgggcgagg ccgcccaaat    3240
ttggcaataa ataaagcttg ggaagcttgg acctgaaaaa aaaaa                    3285
```

<210> SEQ ID NO 3
<211> LENGTH: 16
<212> TYPE: PRT
<213> ORGANISM: Artificial Sequence
<220> FEATURE:
<223> OTHER INFORMATION: CDR derived from non-human source

<400> SEQUENCE: 3

Arg Ser Ser Gln Ser Ile Val His Ser Asn Gly Asn Thr Tyr Leu Gln
1               5                   10                  15

<210> SEQ ID NO 4
<211> LENGTH: 7
<212> TYPE: PRT
<213> ORGANISM: Artificial Sequence
<220> FEATURE:
<223> OTHER INFORMATION: CDR derived from non-human source

<400> SEQUENCE: 4

Lys Val Ser Asn Arg Leu Tyr
1               5

<210> SEQ ID NO 5
<211> LENGTH: 9
<212> TYPE: PRT
<213> ORGANISM: Artificial Sequence
<220> FEATURE:
<223> OTHER INFORMATION: CDR derived from non-human source

<400> SEQUENCE: 5

Phe Gln Gly Ser His Val Pro Trp Thr
1               5

<210> SEQ ID NO 6
<211> LENGTH: 6
<212> TYPE: PRT
<213> ORGANISM: Artificial Sequence
<220> FEATURE:
<223> OTHER INFORMATION: CDR derived from non-human source

<400> SEQUENCE: 6

Gly Gly Tyr Leu Trp Asn
1               5

<210> SEQ ID NO 7
<211> LENGTH: 16
<212> TYPE: PRT
<213> ORGANISM: Artificial Sequence
<220> FEATURE:
<223> OTHER INFORMATION: CDR derived from non-human source

<400> SEQUENCE: 7

Tyr Ile Ser Tyr Asp Gly Thr Asn Asn Tyr Lys Pro Ser Leu Lys Asp
1               5                   10                  15

<210> SEQ ID NO 8
<211> LENGTH: 8
<212> TYPE: PRT
<213> ORGANISM: Artificial Sequence
<220> FEATURE:
<223> OTHER INFORMATION: CDR derived from non-human source

<400> SEQUENCE: 8

```
Tyr Gly Arg Val Phe Phe Asp Tyr
1               5
```

<210> SEQ ID NO 9
<211> LENGTH: 112
<212> TYPE: PRT
<213> ORGANISM: Artificial Sequence
<220> FEATURE:
<223> OTHER INFORMATION: anti-IGF1R immunoglobulin

<400> SEQUENCE: 9

```
Asp Val Leu Met Thr Gln Ile Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Gln Trp Tyr Leu Gln Lys Pro Gly Gln Ser
        35                  40                  45

Pro Lys Leu Leu Ile Tyr Lys Val Ser Asn Arg Leu Tyr Gly Val Pro
    50                  55                  60

Asp Arg Phe Ser Gly Ser Gly Ser Gly Thr Asp Phe Thr Leu Lys Ile
65                  70                  75                  80

Ser Ser Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110
```

<210> SEQ ID NO 10
<211> LENGTH: 112
<212> TYPE: PRT
<213> ORGANISM: Artificial Sequence
<220> FEATURE:
<223> OTHER INFORMATION: anti-IGF1R immunoglobulin
<220> FEATURE:
<221> NAME/KEY: VARIANT
<222> LOCATION: (35)..(35)
<223> OTHER INFORMATION: any amino acid
<220> FEATURE:
<221> NAME/KEY: VARIANT
<222> LOCATION: (36)..(36)
<223> OTHER INFORMATION: any amino acid
<220> FEATURE:
<221> NAME/KEY: VARIANT
<222> LOCATION: (39)..(39)
<223> OTHER INFORMATION: any amino acid
<220> FEATURE:
<221> NAME/KEY: VARIANT
<222> LOCATION: (99)..(99)
<223> OTHER INFORMATION: any amino acid

<400> SEQUENCE: 10

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asp Gly Xaa Xaa Tyr Leu Xaa Trp Tyr Leu Gln Lys Pro Gly Gln Ser
        35                  40                  45

Pro Gln Leu Leu Ile Tyr Leu Val Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Xaa Pro Arg Thr Phe Gly Gln Gly Thr Lys Val Glu Ile Lys
```

<210> SEQ ID NO 11
<211> LENGTH: 112
<212> TYPE: PRT
<213> ORGANISM: Artificial Sequence
<220> FEATURE:
<223> OTHER INFORMATION: anti-IGF1R immunoglobulin

<400> SEQUENCE: 11

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Gln Trp Tyr Leu Gln Lys Pro Gly Gln Ser
        35                  40                  45

Pro Gln Leu Leu Ile Tyr Lys Val Ser Asn Arg Leu Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Val Glu Ile Lys
            100                 105                 110
```

<210> SEQ ID NO 12
<211> LENGTH: 117
<212> TYPE: PRT
<213> ORGANISM: Artificial Sequence
<220> FEATURE:
<223> OTHER INFORMATION: anti-IGF1R immunoglobulin

<400> SEQUENCE: 12

```
Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Gly Gly
            20                  25                  30

Tyr Leu Trp Asn Trp Ile Arg Gln Phe Pro Gly Asn Lys Leu Glu Trp
        35                  40                  45

Met Gly Tyr Ile Ser Tyr Asp Gly Thr Asn Asn Tyr Lys Pro Ser Leu
    50                  55                  60

Lys Asp Arg Ile Ser Ile Thr Arg Asp Thr Ser Lys Asn Gln Phe Phe
65                  70                  75                  80

Leu Lys Leu Asn Ser Val Thr Asn Glu Asp Thr Ala Thr Tyr Tyr Cys
                85                  90                  95

Ala Arg Tyr Gly Arg Val Phe Phe Asp Tyr Trp Gly Gln Gly Thr Thr
            100                 105                 110

Leu Thr Val Ser Ser
        115
```

<210> SEQ ID NO 13
<211> LENGTH: 117
<212> TYPE: PRT
<213> ORGANISM: Artificial Sequence
<220> FEATURE:
<223> OTHER INFORMATION: anti-IGF1R immunoglobulin

<400> SEQUENCE: 13

```
Gln Val Gln Leu Gln Glu Ser Gly Pro Gly Leu Val Lys Pro Ser Glu
1               5                   10                  15
```

```
Thr Leu Ser Leu Thr Cys Thr Val Ser Gly Tyr Ser Ile Thr Gly Gly
            20                  25                  30

Tyr Leu Trp Asn Trp Ile Arg Gln Pro Pro Gly Lys Gly Leu Glu Trp
            35                  40                  45

Met Gly Tyr Ile Ser Tyr Asp Gly Thr Asn Asn Tyr Lys Pro Ser Leu
 50                  55                  60

Lys Asp Arg Ile Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Tyr Gly Arg Val Phe Phe Asp Tyr Trp Gly Gln Gly Thr Leu
            100                 105                 110

Val Thr Val Ser Ser
            115

<210> SEQ ID NO 14
<211> LENGTH: 117
<212> TYPE: PRT
<213> ORGANISM: Artificial Sequence
<220> FEATURE:
<223> OTHER INFORMATION: anti-IGF1R immunoglobulin

<400> SEQUENCE: 14

Gln Val Gln Leu Gln Glu Ser Gly Pro Gly Leu Val Lys Pro Ser Glu
 1               5                  10                  15

Thr Leu Ser Leu Thr Cys Thr Val Ser Gly Tyr Ser Ile Thr Gly Gly
            20                  25                  30

Tyr Leu Trp Asn Trp Ile Arg Gln Pro Pro Gly Lys Gly Leu Glu Trp
            35                  40                  45

Ile Gly Tyr Ile Ser Tyr Asp Gly Thr Asn Asn Tyr Lys Pro Ser Leu
 50                  55                  60

Lys Asp Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Tyr Gly Arg Val Phe Phe Asp Tyr Trp Gly Gln Gly Thr Leu
            100                 105                 110

Val Thr Val Ser Ser
            115

<210> SEQ ID NO 15
<211> LENGTH: 117
<212> TYPE: PRT
<213> ORGANISM: Artificial Sequence
<220> FEATURE:
<223> OTHER INFORMATION: anti-IGF1R immunoglobulin

<400> SEQUENCE: 15

Gln Val Gln Leu Gln Glu Ser Gly Pro Gly Leu Val Lys Pro Ser Glu
 1               5                  10                  15

Thr Leu Ser Leu Thr Cys Thr Val Ser Gly Tyr Ser Ile Ser Gly Gly
            20                  25                  30

Tyr Leu Trp Asn Trp Ile Arg Gln Pro Pro Gly Lys Gly Leu Glu Trp
            35                  40                  45

Ile Gly Tyr Ile Ser Tyr Asp Gly Thr Asn Asn Tyr Lys Pro Ser Leu
 50                  55                  60

Lys Asp Arg Val Thr Ile Ser Val Asp Thr Ser Lys Asn Gln Phe Ser
```

```
                65                  70                  75                  80
Leu Lys Leu Ser Ser Val Thr Ala Ala Asp Thr Ala Val Tyr Tyr Cys
                    85                  90                  95

Ala Arg Tyr Gly Arg Val Phe Phe Asp Tyr Trp Gly Gln Gly Thr Leu
                100                 105                 110

Val Thr Val Ser Ser
        115

<210> SEQ ID NO 16
<211> LENGTH: 17
<212> TYPE: PRT
<213> ORGANISM: Homo sapiens

<400> SEQUENCE: 16

Glu Asn Lys Leu Pro Glu Pro Glu Glu Leu Asp Leu Glu Pro Glu Asn
1               5                   10                  15

Met
```

METHODS FOR THE IDENTIFICATION AND TREATMENT OF PATIENTS SENSITIVE TO ANTI IGF-1R INHIBITION THERAPY

BACKGROUND OF THE INVENTION

In a cancer cell, receptor tyrosine kinases (TK) play important role in connecting the extra-cellular tumor microenvironment to the intracellular signaling pathways that control diverse cellular functions, such as, cell division cycle, survival, apoptosis, gene expression, cytoskeletal architecture, cell adhesion, and cell migration.

The type I insulin like-growth factor receptor (IGF-1R, CD221) belongs to receptor tyrosine kinase (RTK) family, (Ulrich et al., Cell.; 61:203-12 (1990)). Insulin-like growth factors (IGFs), e.g., IGF-I and IGF-II have been implicated in the acquisition of an invasive and metastatic tumor phenotype [Baserga, Cell., 79:927-30 (1994); Baserga et al., Exp. Cell Res., 253:1-6 (1999) and Baserga et al., Int. J. Cancer., 107: 873-77 (2003)]. There is a large body of literature on the actions and activities of IGFs (IGF-1, IGF-2, and IGF variants). See Van Wyk et al., Recent Prog. Horm. Res., 30: 259 (1974); Binoux, Ann. Endocrinol., 41: 157 (1980); Clemmons and Van Wyk, Handbook Exp. Pharmacol., 57: 161 (1981); Baxter, Adv. Clin. Chem., 25:49 (1986); U.S. Pat. No. 4,988,675; WO 91/03253; WO 93/23071). Each of these growth factors exerts its mitogenic effects by binding to a common receptor named the insulin-like growth factor receptor-1 (IGF-1R) (Sepp-Lorenzino, Breast Cancer Research and Treatment 47:235 (1998)); Klapper, et al., Endocrinol. 112:2215 (1983) and Rinderknecht, et al., Febs. Lett. 89:283 (1978)), which is closely related to the insulin receptor (IR) in structure and shares some of its signaling pathways (Jones and Clemmons, Endocr. Rev., 16: 3-34 (1995); Ulrich et al., Cell 61: 203 212, (1990)).

The molecular architecture of IGF-1R comprises, two extra-cellular α subunits (130-135 kD) and two membrane spanning β subunits (95 kD) that contain the cytoplasmic catalytic kinase domain. IGF-1R, like the insulin receptor (InsR), differs from other RTK family members by having covalent dimeric (α2β32) structures. Structurally, IGF-1R is highly related to InsR (insulin receptor) (Pierre De Meyts and Whittaker, Nature Reviews Drug Discovery.; 1: 769-83 (2002); Ulrich et al., EMBO J., 5:2503-12 (1986); Blakesley et al., Cytokine Growth Factor Rev., 7:153-56 (1996)). Insulin-like growth factor-I (IGF-I) is a 7649-dalton polypeptide with a pI of 8.4 that circulates in plasma in high concentrations and is detectable in most tissues (Rinderknecht and Humbel, Proc. Natl. Acad. Sci. USA, 73: 2365 (1976); Rinderknecht and Humbel, J. Blol. Chem., 253: 2769 (1978)). The binding of IGF-1 and IGF-2 to the a chain induces conformational changes that result in auto-phosphorylation of each β-chain at specific tyrosine residues, converting the receptor from unphoshorylated state to the active state. The activation of three tyrosine residues in the activation loop (Tyr residues at 1131, 1135 and 1136) of the kinase domain leads to increase in catalytic activity that triggers docking and phosphorylation of the substrates such as IRS-1 and Shc adaptor proteins. Activation of these substrates leads to phosphorylation of additional proteins involved in the signaling cascade of survival (PI3K, AKT, TOR, S6) and/or proliferation (mitogen-activated protein kinase, p42/p44) (Pollak et al., Nature Reviews Cancer.; 4:505-516 (2004); Baserga et al., Biochem Biophys Act.; 1332:F105-F126 (1997); Baserga et al., Int. J. Cancer.; 107:873-77 92003)).

There is considerable evidence for a role for IGF-I and/or IGF-IR in the maintenance of tumor cells in vitro and in vivo (Baserga, Cancer Res., 55:249-252 (1995); for a review, see Khandwala et al., Endocr. Rev. 21: 215-244 (2000)); Daughaday and Rotwein, Endocrine Rev., 10:68-91 (1989); Sell C. et al., Proc. Natl. Acad. Sci., USA, 90: 11217-11221 (1993); Sell C. et al., Mol. Cell. Biol., 14:3604-3612 (1994); Morrione A. J., Virol., 69:5300-5303 (1995)). For example, individuals with "high normal" levels of IGF-I have an increased risk of common cancers compared to individuals with IGF-I levels in the "low normal" range (Rosen et al., Trends Endocrinol. Metab. 10: 136-41, 1999). For a review of the role IGF-I/IGF-I receptor interaction plays in the growth of a variety of human tumors, see Macaulay, Br. J. Cancer, 65: 311 320, (1992). Overexpression of IGF-1R has also been demonstrated in several cancer cell lines and tumor tissues—IGF-1R is overexpressed in 40% of all breast cancer cell lines (Pandini, et al., Cancer Res.; 5:1935 (1999)) and in 15% of lung cancer cell lines. In breast cancer tumor tissue, it is overexpressed 6-14 fold. Likewise, ninety percent of colorectal cancer tissue biopsies exhibit elevated IGF-1R levels, wherein the extent of IGF-1R expression is correlated with the severity of the disease. Analysis of primary cervical cancer cell cultures and cervical cancer cell lines revealed 3- and 5-fold overexpression of IGF-1R, respectively, as compared to normal ectocervical cells (Steller, et al., Cancer Res.; 56:1762 (1996)). Expression of IGF-1R in synovial sarcoma cells also correlated with an aggressive phenotype (i.e., metastasis and high rate of proliferation; Xie, et al., Cancer Res.; 59:3588-9 (1999)).

Other arguments in favor of the role of IGF-IR in carcinogenesis come from studies using murine monoclonal antibodies directed against the receptor or using dominant negative forms of IGF-IR. In effect, murine monoclonal antibodies directed against IGF-IR inhibit the proliferation of numerous cell lines in culture and the growth of tumor cells in vivo ([Arteaga C. et al., Cancer Res.; 49:6237-6241 (1989); Li et al., Biochem. Biophys. Res. Com.; 196:92-98 (1993); Scotlandi K et al., Cancer Res., 58:4127-4131 (1998)0. Likewise, Jiang et al., Oncogene, 18:6071-6077 (1999) has demonstrated that a negative dominant of IGF-IR is capable of inhibiting tumor proliferation.

IGF-1R-specific antibodies are described in one or more of the following publications—WO 2003/100008); WO 2002/53596; WO 2004/71529); WO 2003/59951); WO 2004/83248); WO 2003/106621); WO 2004/87756). See also Burtrum et. al. Cancer Research 63:8912-8921 (2003).

In years past, IGF-IR has become an attractive molecular target for cancer treatment given as it is expressed in a wide range of tumors (Renato Baserga, Experimental Cell Research, 315: 727-732 (2009). Several studies indicate that IGF-IR activation is associated with the growth, invasion, and metastasis of breast cancer including the observation that the expression of constitutively active IGF-IR in the mammary gland leads to the development of tumors while overexpression of a constitutively activated IGF-IR is sufficient to cause transformation of immortalized human mammary epithelial cells and growth in immunocompromised mice. Emerging data suggest that IGF-IR signaling is important for the development of breast tumors and cancers continue to depend upon this pathway for sustained growth and survival (Ryan et al., The emerging role of the insulin-like growth factor pathway as a therapeutic target in cancer.; Oncologist; 13:16-24 (2008).

The IGF-IR pathway is also implicated in resistance to targeted therapies including those that target the ER and the epidermal growth factor receptor (EGFR) family members EGFR and HER2. For example, IGF-IR is reportedly up-regulated during the acquisition of tamoxifen resistance.

According to published data, continuous exposure of MCF-7 cells to tamoxifen resulted in the eventual emergence of resistant cells, called MCF-7 Tam-R, which use IGF-IR for their growth (Knowlden et al., Insulin-like growth factor-I receptor signaling in tamoxifen-resistant breast cancer: a supporting role to the epidermal growth factor receptor.; *Endocrinology;* 146:4609-18 (2005). Likewise, activation of the IGF-IR signaling cascade has also been reported in models of resistance to agents that target the EGFR family. Jennifer H. Law; *Cancer Research* 68: 10238 (2008), doi: 10.1158/0008-5472.CAN-08-2755; Jones et al.; *Endocr. Relat. Cancer;* 11:793-814 (2004).; Lu Y et al., Insulin-like growth factor-I receptor signaling and resistance to trastuzumab (Herceptin).; *J Natl Cancer Inst;* 93:1852-7 (2001)0 As a consequence, use of IGF-1R pathway inhibitors appears to be justified in order to prevent or attenuate the development of resistance. See Jennifer Law, supra; Knowlden et al., *Breast Cancer Res Treat,* 111:79-91 (2008)).

Agents, such as those noted supra, are expected to decrease IGF-1R function and/or expression and thus may be effective in treating patents presenting with IGF-1R mediated pathologies. However, it is expected that a portion of cancer patients may not respond to such treatments or may need to be monitored over time while being treated with an IGF-1R inhibitor.

As a consequence, there is a need in the art for methods for not only identifying specific cancer populations likely to present with or at risk of developing an IGF-1R pathology but also a need for predicting a patient's probable outcome to treatment with or response to one or more anti-cancer therapies that target IGF-1R, e.g., sensitivity or resistance to treatment with an IGF-1R inhibitor.

In the past decade, LKB1 (STK11) has generated significant interest especially when studies showed that it is defective in patients with Peutz-Jeghers syndrome (PJS). Specifically, inactivating mutations, exonic deletions and whole gene deletions in Lkb1 were found in most PJS syndrome patients. [Hezel et al., *Oncogene;* 27: 6908-6919 (2008); Volikos et al.; *J Med Genet;* 43: e18 (2006); WO/2009/102986.] The type and pattern of these mutations have been extensively reviewed elsewhere. [Alessi et al., *Annu Rev Biochem* 75: 137-163 (2006); Launonen V., *Hum Mutat.;* 26: 291-297 (2005).] PJS is characterized by; (1) muco-cutaneous hyperpigmentation involving the lips and hands, (2) the early development of hamartomas, which are well-differentiated vascular polyps found throughout the gastrointestinal tract beginning at an early age and (3) an increased incidence of carcinomas [Westerman et al., *Lancet* 353: 1211-1215 (1999)]. Researchers have identified more than 140 mutations in the LBK1 gene that are responsible for Peutz-Jeghers syndrome. Many of these mutations result in the production of an abnormally short, nonfunctional version of the serine/threonine kinase 11 enzyme. Other mutations change a single protein building block (amino acid) used to build the enzyme. Research has shown that the loss of this enzyme's function allows cells to divide too often, leading to the formation of polyps in the gastrointestinal tract. Sometimes these polyps develop into malignant (cancerous) tumors. Among the most important associated health-related concerns is the increased risk of cancer development Sanchez-Cespedes M., *Oncogene;* 26:7825-7832 (2007). While gastrointestinal tumors are the most commonly diagnosed malignancies in PJS patients, the risk of developing cancer from other origins is also significantly higher. [Sanchez-Cespedes M supra; A Hemminki., *Cell. Mol. Life Sci.;* 55: 735-750 (1999)].

LKB1 is a ubiquitously expressed gene, which encodes a serine/threonine kinase. There is only a single isoform of the LKB1 gene in the human genome, which spans 23 kb and is made up of nine coding exons and a final noncoding exon. The LKB1 gene maps to the chromosomal region 19p13.3, which is frequently lost in several types of cancer. The gene is transcribed in a telomere-to-centromere direction and encodes for a protein of 433 amino acids and approximately 48 kDa (Hemminki et al., *Nature* 391, 184-187 (1998)]. The protein possesses a nuclear localization signal in the N-terminal noncatalytic region (residues 38-43) and a kinase domain (residues 49-309) [Alessi et al., *Annu Rev Biochem* 75: 137-163 (2006)]. A putative prenylation motif (CAAX-box) is located within the C-terminus. [Launonen V., *Hum Mutat* 26: 291-297 (2005); Alessi, supra]. Although LKB1 protein expression is mainly cytoplasmic, it can also be localized in the nucleus. LKB1 is a master kinase that activates a family of 14 kinases related to AMPK [adenosine monophosphate (AMP)-activated protein kinase] suggesting that it may contribute to tumorigenesis and metastasis through mechanisms other than AMPK regulation (Hemminki, supra).

A review of the literature informs of a total of 40 different somatic LKB1 mutations in 41 sporadic tumors and seven cancer cell lines. Most of the somatic LKB 1 mutations result in truncation of the protein. The loss of the enzyme's tumor suppressor function likely underlies the increased risk of gastrointestinal tumors, breast cancer, and other forms of cancer in PJS patients. Mutations occur particularly in lung and colorectal cancer. Of significant import is the observation that PJS patients are at an increased risk of developing malignancies in epithelial tissues—for example it has been estimated that there is about 84, about 213 and about 520 fold increased risk of developing colon, gastric and small intestinal cancers respectively. PJS patients are also at an increased risk of developing cancers in the breast, lung, ovaries, uterus, cervix and testes. To date, 144 different mutations in LKB1 have been identified in PJS patients and sporadic cancers, [Alessi, supra.] Somatic mutations in LKB1 are observed in sporadic pulmonary, pancreatic and biliary cancers and melanomas. [A F Hezel, *Oncogene* 27, 6908-6919 (2008)]. Individuals with PJS are also at increased risk for intestinal and extraintestinal malignancies. Colorectal and gastric cancers can arise from adenomas that are commonly found in individuals with PJS. The risk for pancreatic cancer is also greatly increased over the population risk [Giardiello et al., *N Engl J Med.;* 316: 1511-4 (1987). The same holds true for neuroendocrine lung cancers. [Amin et al., *Pathol Int;* 58: 84-88 (2008)].

Recent studies have demonstrated that loss of LKB1 is associated with invasiveness and metastasis in breast, lung, and endometrial adenocarcinomas [Zhao et al.; *Cancer Cell.* 3:483-495 (2003); Contreras et al., *Cancer Res.* 68:759-766 (2008)]. For example, LKB1 is one of the most commonly mutated genes in sporadic human lung cancer, particularly in multiple subtypes of non-small cell lung carcinoma (NSCLC), where at least 15 to 35% of cases have this lesion. [Sanchez-Cespedes M, et al., *Cancer Res.;* 62:3659-3662 (2002); David B. Shackelford, *Nature Reviews Cancer* 9:563-575 (2009); Ji, H. et al., *Nature* 448:807-810 (2007).]. The mutational pattern of LKB1 in lung tumors of sporadic origin is that of a classical tumor-suppressor gene. First of all, mutations are homozygous, as predicted by Knudson's two hit hypothesis. Second, a large proportion of mutations lead to the generation of truncated proteins, indicative of an inactivating event. Third, the mutations in tumors of sporadic origin arise somatically, and so are only present in the tumor tissue. See Sanchez-Cespedes M., *Oncogene,* 26:7825-7832 (2007) for a list of the alterations found in LKB1 relative to lung cancer.

The data also show that LKB1 is somatically mutated in 20% of cervical carcinomas, making it the first known recurrent genetic alteration for this tumor type. [Wingo et al., PLoS ONE 4(4): e5137. (2009); doi:10.1371/journal.pone.0005137; Robert Shaw; *Sci. Signal.*, 2:pe55 (2009)]. Females with PJS are also at risk for ovarian sex cord tumors with annular tubules (SCTAT), mucinous tumors of the ovaries and fallopian tubes and adenoma malignum of the cervix, a rare aggressive cancer. Males occasionally develop calcifying Sertoli cell tumors of the testes, which secrete estrogen and can lead to gynecomastia. [Young et al., *Mod Pathol.*; 2: S81-98 (2005).]

LKB1 promoter hypermethylation has been reported in nearly 50% of sporadic papillary breast cancers and 12% of testicular cancers, whereas LKB1 promoter hypermethylation appears uncommon or absent in other types of sporadic breast cancers, as well as colon, gastric and pancreatic cancers [Esteller et al., *Oncogene;* 19: 164-168 (2000)]. Additionally, loss of LKB1 expression has been noted in sporadic endometrial cancers as well. [Contreras et al.; *Cancer Res* 68: 759-766 (2008)].

Cancer as a disease contributes to a major financial burden to the community and to individuals. It accounts for nearly one-quarter of deaths in the United States, exceeded only by heart diseases. Although conventional histological and clinical features have been correlated to prognosis, the same apparent prognostic type of tumor varies widely in its responsiveness to therapy and consequent survival of the patient. In addition, accurate prognosis as well as a determination of treatment outcome vary broadly across most cancer types.

As a consequence, a great deal of effort is being directed to using new technologies to find new classes of biomarkers, which is becoming one of the highly prized targets of cancer research. See Petricoin et al, Nature Reviews Drug Discovery, 1: 683-695 (2002); Sidransky, Nature Reviews Cancer, 2: 210-219 (2002). Accompanying the increased knowledge about biomarkers is an increased appeal of the use of biomarkers as predictive or risk assessment entities. Scientists believe that the development of new validated risk-assessment biomarkers will lead to significant reductions in healthcare and drug development costs as well as provide a tool for achieving successful preventive intervention. Within clinical research, oncology is expected to have the largest gains from biomarkers over the next five to ten years. Development of personalized medicine for cancer is closely linked to biomarkers, which may serve as the basis for diagnosis, drug discovery and monitoring of diseases. Jain K K. Curr Opin Mol Ther. 2007 December; 9(6):563-71 (2007).

However, the ability to predict drug sensitivity in patients is particularly challenging especially in IGF-1R mediated disorders because the extensive histoclinical heterogeneity attendant such cancers often times cause differential response to anti-cancer drugs, thus resulting in a diversity of chemosensitivity in cancer cells.

Examples of biomarkers include genetic markers (e.g., nuclear aberrations [such as micronuclei], gene amplification, and mutation), cellular markers (e.g., differentiation markers and measures of proliferation, such as thymidine labeling index), histologic markers (e.g., premalignant lesions, such as leukoplakia and colonic polyps), and biochemical and pharmacologic markers (e.g., ornithine decarboxylase activity). The first demonstration of molecular signatures in oesophageal cancer that correlate with treatment response is detailed in Luthra, R. et al.; Gene expression profiling of localized esophageal carcinomas: association with pathologic response to preoperative chemoradiation.; *J. Clin. Oncol.* 12 Dec. 2005 (10.1200/jco.2005.03.3688).

Other studies have used gene expression profiling to analyze various cancers, and those studies have provided new diagnosis and prognosis information in the molecular level. See Zajchowski et al.,—'Identification of Gene Expression Profiled that Predict the Aggressive Behavior of Breast Cancer Cells," Cancer Res. 61:5168 (2001); West et al, "Predicting the Clinical Status of Human Breast Cancer by Using Gene Expression Profiles," Proc. Natl. Acad. Sc. U.S.A. 98:11462 (2001); van't Veer et al., "Gene Expression Profiling Predicts the Outcome of Breast Cancer," Nature 415:530 (2002); Roberts et al., "Diagnosis and Prognosis of Breast Cancer Patients," WO 02/103320; Sorlie et al, Proc. Natl. Acad. Sc U.S.A. 100:8418 (2003); Perou et. al., Nature 406: 747 (2000); Khan et al, Cancer Res 58, 5009 (1998); Golub et al, Science 286, 531 (1999); Alizadeh et al, Nature 403, 503 (2000). Methods for the identification of informative genesets for various cancers have also been described. See Roberts et al., "Diagnosis and Prognosis of Breast Cancer Patients," WO 02/103320; Golub et al, U.S. Pat. No. 6,647,341.

Current predictive and prognostic biomarkers include DNA ploidy, S-phase, Ki-67, Her2/neu (c-erb B-2), p53, p21, the retinoblastoma (Rb) gene, MDR-1, bcl-2, cell adhesion molecules, blood group antigens, tumor associated antigens, proliferating antigens, oncogenes, peptide growth factors and their receptors, tumor angiogenesis and angiogenesis inhibitors, and cell cycle regulatory proteins. Beta human chorionic gonadotropin (J3-hCG), carcinoembryonic antigen, CA-125, CA 19-9, and others have been evaluated and shown to correlate with clinical response to chemotherapy. See de Vere White et al., *Oncology,* 12(12):1717-23 (1998); Stein, J. P. et al., "Prognostic markers in bladder cancer: a contemporary review of the literature" *J. Urol.;* 160 (3 Pt 1):645-59 (1998); Cook, A. M. et al., "The utility of tumour markers in assessing the response to chemotherapy in advanced bladder cancer" *Proc. Annu. Meet. Am. Soc. Clin. Oncol.,* 17:1199 (1998).

In the case of cancer, molecular markers such as the level of HER2/neu, p53, BCL-2 and estrogen/progesterone receptor expression have been clearly shown to correlate with disease status and progression. This example demonstrates the value of diagnostic and prognostic markers in cancer therapy. Reports from retrospective studies have shown that multivariate predictive models combining existing tumor markers improve cancer detection. See van Haaften-Day C. et al., "OVX1, macrophage-colony stimulating factor, and CA-125-II as tumor markers for epithelial ovarian carcinoma: a critical appraisal", *Cancer* (Phila), 92: 2837-44, (2001). These findings bring hope that cancer treatment will be vastly improved by better predicting the response of individual tumors to therapy.

Consequently, while a central paradigm in the care and treatment of patients presenting with cellular proliferative disorders mediated by IGF-1R is to offer better risk assessment, screening, diagnosis, prognosis and selection and monitoring of therapy, the current state of art, nevertheless, paints a grim picture relative to prognostic biomarkers useful for tailoring a therapeutic protocol involving an IGF-1R inhibitor (IGF-1Ri). The identification of predictive biomarkers is thus an essential precondition for the further development of personalized medicine The term biomarker refers not only to biological parameters measured directly from clinical diagnosis, gene diagnostics, etc., but also computation methods which allow for predictions to be made from suitable measured values of biological parameters, or make it possible to calculate a prognosis for the clinical response to a therapy. As indicated elsewhere, the finding of such complex biomarkers in practice is often extremely unreliable or even impossible owing to the great variety of possible biological parameters, which often exceeds significantly the number of subjects in clinical studies.

Previous studies have reported on the expression of IGF1-R, phospho-IGF-IR, insulin receptor substrates-1 (IRS1), and -2 (IRS2), and predictive gene expression signatures. See, for example, Cao et al., *Cancer Res*, 68:8039-48 (2008), Huang F et al., The mechanisms of differential sensitivity to an insulin-like growth factor-1 receptor inhibitor (BMS-536924) and rationale for combining with EGFR/HER2 inhibitors. Cancer Res.; 69:161-70 (2009); Byron et al., Insulin receptor substrates mediate distinct biological responses to insulin-like growth factor receptor activation in breast cancer cells. British J. Cancer; 95:1220-8 (2006). Thus, while insulin-like growth factor-1 receptor (IGF-1R), epidermal growth factor receptor (EGFR), and HER2 expressions have been reported to correlate with clinical outcomes in several solid tumors, the clinical significance of these biomarkers remains unclear. Indeed as late as 2007, investigators have argued for a better understanding of the clinical implications of risk assessment or prognostic biomarkers; e.g., predicting sensitivity of IGF-1R expressing cells to an IGF-1R inhibitor. See for example Matsubara et al., *Journal of Clinical Oncology*, 2007 ASCO Annual Meeting Proceedings (Post-Meeting Edition); 25 (18S); 4539 (2007), whose work suggests that IGF-1R expression in surgical gastric cancer specimens may predict poor outcomes in postoperative patients with gastric cancer. (emphasis supplied). Similar conclusions have been reached by other investigators relative to predicting treatment response to an IGF-1R inhibitor. Similarly, Zha J et al. provide an intriguing report detailing a comprehensive preclinical evaluation of predictive biomarkers for h10H5 (Genentech, South San Francisco, Calif.), a humanized monoclonal antibody to IGF-IR. Lead investigators argue that the identification of such biomarkers remains arguably the most important issue in development of drugs targeting IGF-IR. [Molecular predictors of response to a humanized anti-insulin-like growth factor-I receptor monoclonal antibody in breast and colorectal cancer. Mol Canc Ther 2009; 8:2110-21 (2009).]

In sharp contrast, Carden et al., Predictive biomarkers for targeting insulin-like growth factor-I (IGF-I) receptor; Mol. Cancer. Ther., 8: 2077 (2009) provide a detailed assessment of certain elements of the pathway limited to breast and colorectal cancer models, wherein the authors conclude that for sensitivity to h10H5 their data suggested that IGF2, IRS1, and IRS2 protein expression may be important for patient selection. (Emphasis supplied).

In yet another study, investigators have tried to correlate sensitivity of NSCLC cell lines to treatment with a specific IGF-1R antibody-designated R1507 (RO4858696—a fully human IgG1 monoclonal antibody directed against the extracellular portion of the human IGF-1R). Gong et al. report on their attempts to establish the sensitivity to R1507 of 22 NSCLC cell lines, which included 12 adenocarcinomas, 9 squamous cell carcinomas and 1 large cell carcinoma, each of which was examined for known EGFR/KRAS/NRAS/HRAS/PI3K mutations. According to the publication, sensitivity was assessed using a growth inhibition assay that measures a colorimetric signal produced by conversion of resazurin to resorufin, which apparently is directly proportional to the numbers of viable cells. Therein, the authors admit that none of the lines displayed "high sensitivity". The instruction continues that the investigators were unable to calculate the concentration of drug needed to inhibit tumor growth by 50% (GIso) for each line. The instruction continues that the data failed to demonstrate correlation between R1507 sensitivity and lung cancer histology or mutation status. [PLoS One. 2009; 4(10): e7273; "High Expression Levels of Total IGF-1R and Sensitivity of NSCLC Cells In Vitro to an Anti-IGF-1R Antibody (R1507)].

Various attempts in evaluating IGF-1R protein expression in primary tumors from surgically treated NSCLC patients as a potential correlative biomarker utilizing IGF-1R inhibitors have also been described with inconclusive results. For example, Dziadziuszko et al., evaluated IGF1-R expression in tissue microarrays by immunohistochemistry (IHC). The authors discovered that while IGF-1R protein expression was higher in SCC squamous cell carcinomas (SCC), the expression levels of IGF-1R did NOT associate with survival although high IGF-1R gene copy number appeared to associates with better prognosis in operable NSCLC. [*Journal of Clinical Oncology*, 27 (15S): 7524 (2009)]. That IGF-1R expression, determined at the protein level using IHC staining does not represent a prognostic factor in resected NSCLC patients is also evident from studies conducted by F. Cappuzzo et al., *Annals of Oncology Advance Access* published online on Sep. 18, 2009; Annals of Oncology, doi:10.1093/annonc/mdp357.

In light of the above discussion, it is also clear that the art has, so far, failed to appreciate using expression levels of LKB1 as a potential prognostic biomarker useful for tailoring a therapeutic protocol involving an IGF-1R inhibitor.

Taken together, these deficiencies in the art creates a continuing need for innovative strategies that can better predict a patient's sensitivity to treatment or therapy with an IGF-1R inhibitor and inability to tolerate certain medications or treatments. Further, the pre-selection of patients who are likely to respond well to a medicine, drug, or combination therapy may reduce the number of patients needed in a clinical study or accelerate the time needed to complete a clinical development program (M. Cockett et al., *Current Opinion in Biotechnology*, 11:602-609 (2000)).

In sum, new biomarkers for predicting chemosensitivity to IGF-1R inhibitors are highly sought after to improve the current clinical capabilities of IGF-1R inhibitors. Accurate prognosis as well as a determination of treatment outcome with current IGF-1R inhibitors will eventually allow an oncologist to tailor the administration of therapy with patients having poorer prognoses being given the most aggressive treatment. Accurate prediction of treatment outcome, favorable or poor prognosis will also impact clinical trials for new cancer therapies, because potential study patients could then be stratified according to prognostic biomarkers. Further, the pre-selection of patients who are likely to respond well to an IGF-1R inhibitor mono or combination therapy also may reduce the number of patients needed in a clinical study or accelerate the time needed to complete a clinical development program (M. Cockett et al., *Current Opinion in Biotechnology*, 11:602-609 (2000)).

The present invention aims at overcoming the above deficiencies by providing clinically relevant prognostic tools useful in correlating a patient's response to a chemotherapeutic agent able to modulate IGF-1R signaling as well as identifying patients at risk of failing a therapeutic regimen/protocol involving an IGF-1R inhibitor. Towards this end, the present invention identifies a particular biomarker whose profile may be used in a clinical setting including predicting the patients treatment outcome with an IGF-1R targeted therapy. Indeed, it is demonstrated in the examples appearing hereunder that the expression profile of the biomarker is predictive of treatment with an IGF-1R inhibitor, alone or in combination with another therapeutic agent.

SUMMARY OF THE INVENTION

Mounting evidence during the past decade implicates a crucial role of insulin-like growth factor 1 (IGF-1) signaling in development and progression of cancer. The most important single component in this signaling, involving the ligands IGF-1 and IGF-2, several binding proteins, proteases as well as three receptors, is the IGF-1 receptor (IGF-1R). Epidemiological prospective studies have identified high plasma levels of IGF-1 as a potential risk factor for several malignancies [Hankinson et al.; Circulating concentrations of insulin-like growth factor-I and risk of breast cancer, Lancet 351: 1393-1396 (198)]. In addition, IGF-2, whose expression normally is strictly controlled by parental imprinting is upregulated and functions as an important stimulant of the IGF-1R in cancer. [LeRoith et al.; The insulin-like growth factor systems and cancer.; Cancer Lett 195: 127-137 (2003)]. Consequently upregulation of lGF-1R and its ligands appears to define important events for malignant cell growth. More, a unique aspect attendant IGF-1R signaling in cancer is based on several recent findings linking the loss of suppressor oncogenes as well as activation of proto-oncogenes to IGF-1R function and activity. In fact, blockade of IGF-1R has been convincingly shown to cause massive apoptosis of tumour cells in vivo, to inhibit tumorigenesis and block tumour invasion and metastasis. Larsson et al, British Journal of Cancer; 92: 2097-2101 (2005). doi:10.1038/sj.bjc.6602627.

Importantly, early and effective treatment of cancer is fast becoming a critical factor affecting the survival of cancer patients. The selection of treatment regimens against which a cancer is resistant delays the onset of effective treatment of the cancer and can lead to growth and spread of the cancer. This, in turn, can have a negative effect on the patient's treatment outcome. Tumor-specific characteristics that are associated with responsiveness to an anti-cancer agent, e.g., IGF-1R targeted therapeutic, such as the expression of one or more specific genes and/or encoded protein will find use as a prognostic biomarker for identifying potential patients likely to respond or fail treatment with an IGF-1R inhibitor at an earlier stage As a result, patients suffering from tumors expressing such a biomarker can be selected for treatment with an IGF-1R inhibitor. This approach of patient selection has been employed successfully in connection with other cancer treatments. For example, Bunn et al., report selection criteria for patients with non-small cell lung cancer for treatment with an epidermal growth factor receptor (EGFR) tyrosine kinase inhibitor (Clin, Cancer Res. 12: 3652-3656 (2006)). Han at al. identified markers (EGFR mutation, K-ras Mutation and Akt Phosphorylation) pointing to a likelihood of sensitivity to gefitinib (Clin. Cancer Res. 12: 2538-2544 (2006)).

The invention relates to the use of LKB1 expression as a predictive biomarker for identifying responder populations, especially those patients that are likely to be sensitive to treatment with an IGF-1R inhibitor. Responder populations resistant to treatment with an IGF-1R inhibitor are also within the scope of the present invention. The above conclusions are supported by the discovery that decreased expression levels of LKB1 (pre-dose) is predictive of positive treatment outcome with an IGF-1R inhibitor in tumor cells. The data demonstrate that patients exhibiting high levels of LKB1 expression relative to normal are likely to be resistant to treatment with an IGF-1R inhibitor. Conversely, patients presenting with lower than normal expression levels of LKB1 are likely to be sensitive to treatment with an IGF-1R inhibitor (IGF-1Ri). Thus, measurement of LKB1 expression level, gene or protein expression, is particularly useful to identify patients likely to respond to therapy with an IGF-1R inhibitor. The invention also provides methods and procedures for determining patient sensitivity to an IGF-1R inhibiting agent. The invention also provides methods of determining or predicting whether an individual requiring therapy for a disease state such as cancer will or will not respond to treatment, prior to administration of the treatment, wherein the treatment comprises administration of one or more IGF-1R inhibiting agents.

It is noted that while the examples demonstrate use of an IGF-1R inhibitor (MK-0646, DALOTUZUMAB on a lung cancer cell line, the results would apply equally across to other IGF-1R inhibitors—large molecules exemplified by IGF-1R specific antibodies as well as small molecules. Likewise, the therapeutic target is not limited to lung cancer. It includes all cancers that are responsive to treatment with an IGF-1R inhibitor and express the biomarkers detailed herein. For example, IGF-1R signaling has been implicated in lung cancer, breast cancer, prostate cancer, colorectal cancer, sarcoma, multiple myeloma, urinary bladder cancer and other malignancies. [Hartog et al., The insulin-like growth factor 1 receptor in cancer: old focus, new future. Euro J Cancer.; 43:1895-1904 (2007); Sachdev et al., Disrupting insulin-like growth factor signaling as a potential cancer therapy. Mol Cancer Ther.; 6:1-12 (2007)].

In one aspect, the present invention provides, inter alia, a method for treating cancers by pre-selecting patients whose tumors express diminished or low levels of LKB1, thereby increasing the likelihood of a response, in the patient, to therapeutics targeting IGF-1R.

In another aspect, the present invention includes a method of evaluating a response by a mammalian subject to an IGF-1R inhibiting compound which comprises measuring the level of LKB1 in cells of the subject prior to administering the IGF-1Ri and comparing it to a control or reference, wherein patient samples exhibiting low levels of LKB1 relative to the control expression level predict a favorable outcome relative to treatment with an IGF-1Ri.

A method of treating a cellular proliferative disorder mediated by IGFF-1R or responsive to an IGF-1R inhibitor in a selected subject comprising administering to said selected subject a therapeutically effective amount of an IGF-1R inhibiting agent in an amount effective to treat said proliferative disorder, wherein said selected subject has low expression levels of LKB1 prior to administration of said IGF-1R inhibiting agent and wherein low expression levels of LKB1 relative to normal indicates that the selected subject would benefit from treatment with said IGF-1R inhibiting agent.

In another aspect, the invention provides a method for identifying a responder population that is likely to respond therapeutically to treatment with an IGF-1R inhibitor, wherein the method comprises: (a), measuring in a biological sample obtained from a subject suspected of being at risk of or presenting with an IGF-1R mediated disorder the expression level of LKB1; (b) comparing the level obtained in step (a) to the level of expression of said LKB1 in a control sample, wherein a decrease in the level of LKB1 measured in step (a) indicates that the mammal will respond therapeutically to treatment with said IGF-1R inhibitor, whereas an increase in the level of LKB1 relative to normal indicates that the mammal is not likely to respond to treatment or be resistant to treatment with said IGF-1R inhibitor.

The above method may be practiced iteratively over time, wherein decreased levels of LKB1 in the patient sample relative to the control sample suggest a favorable outcome and vice versa. Thus, there is provided a method of monitoring the treatment of a patient having a disease, wherein said disease is treated by a method comprising administering one or more IGF-1R inhibiting agents to the patient. "One or more" IGF-1R inhibiting agents include, for example, a single IGF-1R inhibiting agent used alone or in combination with an anti-cancer agent or a neoplastic agent.

In another aspect, the invention provides a method for predicting whether a mammal will respond therapeutically to a method of treating cancer comprising administering an IGF-1R inhibiting agent, wherein the method comprises: (a), measuring in a biological sample obtained from a patient the expression level of LKB1; (b) comparing the level obtained in step (a) to the level of expression of said LKB1 in a control sample, wherein a decrease the level of LKB1 measured in step (a) indicates that the mammal will respond therapeutically to treatment with said IGF-1R inhibitor, whereas an increase in the level of LKB1 relative to normal indicates that the mammal is not likely to respond to treatment or be resistant to treatment with said IGF-1R inhibitor.

In another embodiment, a method of predicting the sensitivity to treatment with an anti-cancer agent in one of breast cancer, lung cancer, colon cancer, prostate cancer or pancreatic cancer patient is provided. The method comprises obtaining a biological sample from the patient, optionally isolating or purifying mRNA from the biological sample, amplifying the mRNA transcripts by, e.g., RT-PCR, where a lower baseline level of LKB1 (as assessed by, e.g., determining the cycle number at which the fluorescence passes the set threshold level ("ct") of LKB1 mRNA expression) indicates a higher likelihood that the cancer will be sensitive to treatment with the anti-cancer agent.

As used herein, "respond therapeutically" refers to the alleviation or abrogation of the cancer. "Therapeutic response" may be measured by a decrease in cell surface expression. This may mean that the life expectancy of an individual affected with the cancer will be increased or that one or more of the symptoms of the cancer will be reduced or ameliorated. The term encompasses a reduction in cancerous cell growth or tumor volume. Whether a mammal responds therapeutically can be measured by many methods well known in the art, such as pet imaging. Selective IGF-1R inhibition may result in apoptosis of tumor cells, inhibition of tumor formation and/or inhibition of tumor metastasis. [Hartog et al. supra.]

The amount of "decrease" in the level of expression of the invention biomarker e.g., LKB1 measured in the practice of the invention can be readily determined by one skilled in the art including immunoassays and electrophoresis assays. For example, LKB1-specific antibodies are used in a standard immunoassay format to measure LKB1 levels. ELISA (enzyme linked immunosorbent assay) type assays and conventional western blotting assays using e.g. monoclonal antibodies are also envisioned in the practice of the invention. LKB1 levels may also measured by two-dimensional (2-d) gel electrophoresis. 2-d gel electrophoresis is known in the art and typically involves isoelectric focusing (IEF) along a first dimension followed by SDS-page (sodium dodecyl sulphate-polyacrylamide gel electrophoresis) along a second dimension. The resulting electropherograms are analyzed, for example, by immunoblot analysis using antibodies. Suitable antibodies can be produced by known methods or obtained from a commercial source. For the immunoblotting analysis, the antibody does not have to be specific to LKB1 and can be an antibody that is reactive to any form of LKB1.

In one aspect, the decrease in the level of the biomarker is at least a two-fold difference, at least a three-fold difference, or at least a four-fold difference in the level of the biomarker relative to normal. The level of the biomarker can be, for example, the level of protein and/or mRNA transcript of the biomarker—LKB1. Levels of expression of LKB1 may are assayed in a biological sample, e.g., cell lysate, tissue lysate by known methods.

Those of skill in the art are very familiar with differentiating between significant expression of a biomarker, which represents a positive identification, and low level or background expression of a biomarker. Indeed, background expression levels are often used to form a "cut-off" above which increased staining will be scored as significant or positive.

The mammal can be, for example, a human, rat, mouse, dog, rabbit, pig sheep, cow, horse, cat, primate, or monkey.

The method of the invention can be, for example, an in vitro method wherein the step of measuring in the mammal the level of the biomarker comprises taking a biological sample from the mammal and then measuring the level of the biomarker in the biological sample. The biological sample can comprise, for example, at least one of whole fresh blood, peripheral blood mononuclear cells, frozen whole blood, fresh plasma, frozen plasma, urine, saliva, skin, hair follicle, bone marrow, or tumor tissue.

Accordingly, the screening method of the present invention can also be used to stratify a patient population that is most likely to succeed in a treatment protocol comprising an IGF-1R inhibitor, thereby individually selecting and optimizing a therapy for a patient. Factors for consideration in this context include the particular condition being treated, the particular mammal being treated, the clinical condition of the individual patient, the site of delivery of the active compound, the particular type of the active compound, the method of administration, the scheduling of administration, and other factors known to medical practitioners. The therapeutically effective amount of an active compound to be administered will be governed by such considerations, and is the minimum amount necessary to prevent, ameliorate, or treat the disease. Such amount is preferably below the amount that is toxic to the host or which renders the host significantly more susceptible to infections.

The present invention further includes a method of treating a proliferative disease in a mammalian subject, which comprises measuring the level of LKB1 in cells from the subject that exhibits the proliferative disease and administering an IGF-1R inhibiting agent to the subject if the level of LKB1 is lower than that exhibited by normal cells of the same type. In certain embodiment the IGF-1R inhibiting agent is a monoclonal antibody, particularly DALOTUZUMAB™, which described in detail in U.S. Pat. No. 7,241,444, the contents of which are incorporated herein in its entirety.

An alternative embodiment provides a method for treating an IGF-1R mediated cancer or a cancer responsive to treatment with an IGF-1R inhibitor, in a patient, comprising: (a) determining if a cell mediating said cancer is sensitive to an IGF-1R inhibitor, wherein the cell is determined to be sensitive to the inhibitor if the expression levels of LKB1 in said cell is under expressed by said cell relative to expression of the biomarker by an IGF-1R resistant cell or a control cell obtained from a disease free patient; and (b) administering, to said patient, a therapeutically effective amount of an IGF-1R inhibitor if the cell is sensitive.

The invention also provides kits for determining or predicting whether a patient would be susceptible to or resistant to a treatment with an IGF-1R inhibiting agent. The patient may have a cancer or tumor such as, for example, a breast cancer or tumor.

In one aspect, the kit comprises a suitable container that comprises one or more specialized microarrays, one or more IGF-1R inhibiting agents for use in testing cells from patient tissue specimens or patient samples, and instructions for use. The kit may further comprise reagents or materials for monitoring the expression of the invention biomarker at the level of mRNA or protein. In yet another aspect, the invention provides a kit comprising at least one of an antibody and a nucleic acid for detecting the presence of LKB1. In one aspect, the kit further comprises instructions for determining whether or not a mammal will respond therapeutically to a method of treating cancer comprising administering an IGF-1R inhibiting agent.

The invention also provides screening assays for determining if a patient will be susceptible or resistant to treatment with one or more microtubule-stabilizing agents.

The present invention provides a method for assessing whether an IGF-1R inhibitor inhibits in vitro or in vivo growth or survival of a tumor cell comprising determining if said cell underexpresses the LKB1 biomarker relative to a control cell expression of the biomarker, wherein the inhibitor is determined to inhibit said growth or survival if said underexpression is observed. In an embodiment of the invention, expression of the biomarker is assessed by northern blot analysis, real-time polymerase chain reaction (RT-PCR) analysis, western blot analysis, enzyme linked IMMUNOSORBENT assay (ELISA) analysis, radioimmunoassay analysis (RIA), immunohistochemistry or immunofluorescence. In an embodiment of the invention, the patient is human. In an embodiment of the invention the patient has a tumor comprising a cell wherein LKB1 expression is less than that of control cell, e.g., non-tumor cell from same or a different subject is selected. In an embodiment of the invention, LKB1 comprises the nucleotide sequence set forth in SEQ ID NO. 2 or the amino acid sequence as set forth in SEQ ID NO: 1. polarization-related protein LKB1; serine/threonine protein kinase 11. Alternative names for the LKB1 protein may be found at OMIM: 602216; Entrez GeneRIFs: 6794 UNIPROT_SWISSPROT:Q15831. LKB1 gene knockout mice are described in U.S. Pat. No. 6,791,006, which further instructs that while the functional inactivation of the LKB1 gene is related to general sporadic cancers, specific physiological function attendant LKB1 expression in normal cells as well as the mechanism for transforming cells from a normal state to a cancerous state remains a mystery. This reference remains innocently silent concerning a linkage between LKB1 expression and sensitivity to treatment with an IGF-1R inhibitor. Methods of assaying, monitoring and modulating LKB1 activity are described in US 2005-0026233 A1. See also WO2004113562.

Representative antibodies to LKB1 include 3054Phospho-LKB1 (Thr189); 3055 Phospho-LKBl (Ser334); 3050 LKBl (27010-Rabbit mAb) and 3047 LKBl (D60C5-Rabbit mAb) all of which are readily available and described at www.cellsignal.com/products/3482.html, confirmed on Nov. 23,2009. Kits for detecting LKB1 expression are also provided by Cell Signaling Technology, supra.

The amino acid sequence for LKB1 is as set forth in SEQ ID NO:1.

The nucleotide Sequence encoding LKB1 is as set forth in SEQ ID NO:2.

The present invention provides a method for selecting a patient with a tumor responsive to a IGF-1R inhibitor comprising determining if a cell from said tumor underexpresses of the LKB1 biomarker relative to control cell sample or an IGF-1R resistant cell expression of the biomarker; wherein the patient is selected if said underexpression is observed. In an embodiment of the invention, the patient is human. In an embodiment of the invention, the patient has a tumor comprising a cell wherein LKB1 expression is less than that of expression of LKB1 in a resistant cell or a control cell is selected. In an embodiment of the invention, the patient is treated with an IGF-1R inhibitor and, optionally, a further neoplastic or chemotherapeutic or anti-cancer agent. In an embodiment of the invention, the IGF-1R inhibitor is MK-0646. In an embodiment of the invention, the method of treatment comprises an IGF-1R mediated cellular proliferative disorder. In yet another embodiment, the method of treatment comprises treating an IGF-1R responsive disorder. In yet another embodiment, the invention provides a method of treating an IGF-1R mediated disorder with a combination therapy comprising MK-0646 and an anti-cancer agent exemplified by an mTOR inhibitor or an Akt inhibitor. In an embodiment of the invention, the patient is administered the IGF-1R inhibitor in association with a further therapeutic procedure. In an embodiment of the invention, the further therapeutic procedure is one of anti-cancer radiation therapy and surgical tumorectomy. In an embodiment of the invention, the further chemotherapeutic agent is one or more members selected from the group consisting of paclitaxel, gemcitabine, trastuzumab, cisplatin, docetaxel, doxorubicin, melphalan and 5-fluorouracil.

The present invention provides a method for treating a patient with a tumor comprising administering to the patient a therapeutically effective amount of an IGF-1R inhibitor if cells in the tumor underexpress the LKB1 biomarker relative to expression of the biomarker by a cell that is resistant to the inhibitor or a control cell.

The present invention provides a method for treating a patient with a tumor comprising: (a) determining an expression level, by at least one cell in the tumor, of the LKB11 biomarker; and (b) administering, to the patient, a therapeutically effective amount of an IGF-1R inhibitor if LKB1 is underexpressed relative to its expression by a cell that is resistant to the inhibitor and/or a control/reference cell.

The present invention provides a method for predicting whether a patient with a tumor is likely to respond to therapy with a IGF-1R inhibitor comprising determining a level of expression by a cell in the tumor of the LKB1 biomarker, wherein if LKB1 is underexpressed relative to a reference cell or a cell that is resistant to the inhibitor or has acquired resistance to the IGF-1R inhibitor, then the patient is predicted to likely to respond to the inhibitor.

The present invention also provides a method for marketing an IGF-1R inhibitor for treating cancer comprising packaging the inhibitor with a label that recommends use of the inhibitor in a patient having a tumor that underexpresses LKB1 relative to a control or reference cell.

The present invention provides an article of manufacture comprising a IGF-1R inhibitor and a package insert or label that recommends use of the inhibitor in a patient having a tumor that underexpresses LKB1 relative to a control cell.

The present invention provides a screening method to identify tumors responsive to IGF-1R inhibitors, comprising detecting an amount of the LKB1 biomarker in a cell of said tumor, and identifying the tumor as: (i) a IGF-1R inhibitor sensitive tumor if the cell underexpresses said LKB1 biomarker protein relative to a control cell or (ii) a IGF-1R inhibitor resistant tumor if the cell over expresses LKB1 relative to a control cell.

Finally, the invention provides a kit useful for predicting the likelihood of an effective treatment of an IGF-1R mediated cellular proliferative disorder with an IGF-1R inhibiting agent is provided. The kit comprises a solid support, nucleic acids contacting the support, where the nucleic acids are substantially complementary to LKB1 mRNA, and a means for detecting the expression of the mRNA in a biological sample.

In an additional embodiment, the invention provides a kit useful for predicting the likelihood of an effective treatment of an IGF-1R mediated cellular proliferative disorder with an IGF-1R inhibiting agent. The kit comprises a solid support, and a means for detecting the protein expression of LKB1 in a biological sample.

The invention will be better understood upon a reading of the detailed description of the invention when considered in connection with the accompanying figures.

DETAILED DESCRIPTION OF THE INVENTION

Definitions and General Techniques

Figure 1A:
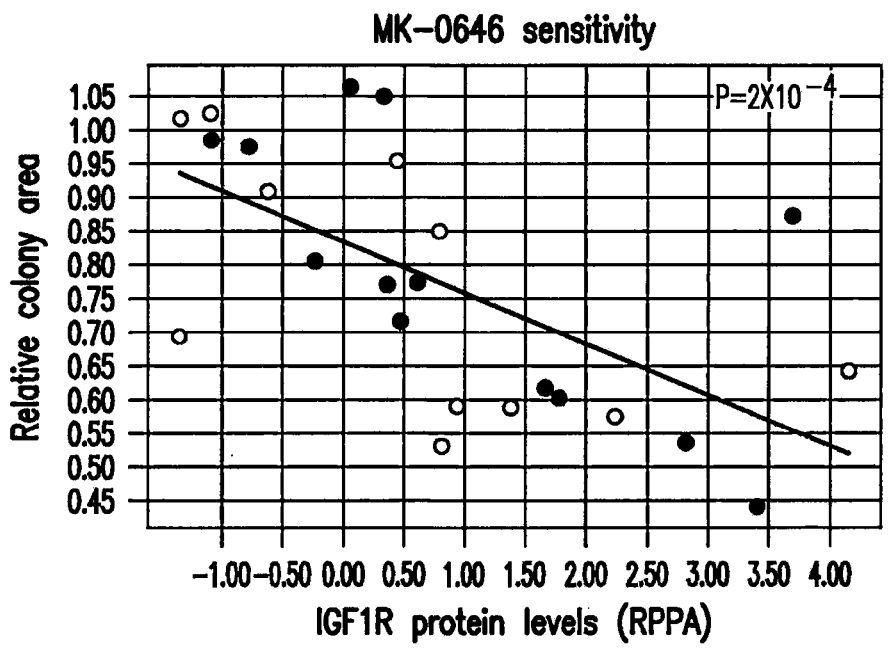
FIG. 1: Relationship between IGF-1R levels and response to MK-0646, erlotinib and the combination in a panel of NSCLC cell lines. Growth inhibition by either MK-0646 (10 ug/ml) or erlotinib (1 uM) or the combination was analyzed under anchorage independent growth using soft agar colony formation assays in 26 NSCLC cell lines comprised of both KRAS mutant or wild type cell lines. A) Relative colony area in MK-0646 treated cell lines (Y-axis) were plotted against IGF-1R protein levels (X-axis) as determined by RPPA analysis. Correlation analysis was performed using Spearman analysis. IGF-1R levels significantly correlation with response to MK-0646 therapy. B) Correlation between IGF-1R mRNA and IGF-1R protein (RPPA). IGF-1R mRNA was determined using gene expression profiling and intensity of IGF-1R probe was correlated with IGF-1R protein levels as determined by RPPA analysis.

The reference works, patents, patent applications, and scientific literature, including accession numbers to GenBank database sequences that are referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter. It is also to be understood that the terminology used herein is for the purpose of describing particular embodiments only, and is not intended to limit the scope of the present invention which will be limited only by the appended claims.

This section presents a detailed description of the many different aspects and embodiments that are representative of the inventions disclosed herein. This description is by way of several exemplary illustrations, of varying detail and specificity. Other features and advantages of these embodiments are apparent from the additional descriptions provided herein, including the different examples. The provided examples illustrate different components and methodology useful in practicing various embodiments of the invention. The examples are not intended to limit the claimed invention. Based on the present disclosure the ordinary skilled artisan can identify and employ other components and methodology useful for practicing the present invention.

It must be noted that as used herein and in the appended claims, the singular forms "a", "and", and "the" include plural referents unless the context clearly dictates otherwise. Thus, for example, reference to "a genetic alteration" includes a plurality of such alterations and reference to "a probe" includes reference to one or more probes and equivalents thereof known to those skilled in the art, and so forth.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the terms "approximately" or "about" in reference to a number are generally taken to include numbers that fall within a range of 5% in either direction (greater than or less than) the number unless otherwise stated or otherwise evident from the context (except where such number would exceed 100% of a possible value). Where ranges are stated, the endpoints are included within the range unless otherwise stated or otherwise evident from the context.

It is contemplated that any embodiment discussed in this specification can be implemented with respect to any method, kit, reagent, or composition of the invention, and vice versa. Furthermore, compositions of the invention can be used to achieve methods of the invention.

All publications mentioned herein are incorporated herein by reference to disclose and describe the methods and/or materials in connection with which the publications are cited.

Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The following terms, unless otherwise indicated, shall be understood to have the following meanings:

A gene or protein marker is "informative" for a condition, phenotype, genotype or clinical characteristic if the expression of the gene marker is correlated with the condition, phenotype, genotype or clinical characteristic to a greater degree than would be expected by chance.

A "biomarker gene" as used herein refers to a DNA, cDNA, mRNA, and/or coding sequence disclosed herein, the expression of which is increased or decreased in transformed cells (i.e., malignant and metastatic cancer cells) as compared to nontransformed cells; or increased or decreased during Contact Normalization as compared to transformed cells not undergoing Contact Normalization. For use in the methods disclosed herein, it is desirable that the biomarker gene is in isolated form and includes polynucleotides encoding a protein and fragments thereof, DNA, RNA, DNA/RNA hybrid, and related molecules, polynucleotides or oligonucleotides complementary to a nucleic acid disclosed herein or a part thereof, and polynucleotides or oligonucleotides that hybridize or bind to a nucleic acid disclosed herein. As used herein, the disclosed gene and gene products are meant to include the genes and gene products specifically described herein and the genes and gene products which are structurally similar variants of the foregoing. Such other genes and gene products will generally have coding sequences that are highly homologous to the coding sequences disclosed herein, and preferably will share at least about 50% amino acid identity and at least about 60% amino acid identity (using BLAST criteria), more desirably sharing 70%, 80%, 90%, 95% or 99% amino acid sequence identity (using BLAST criteria). Biomarkers can be used clinically to screen for, diagnose or monitor the activity of diseases and to guide molecularly targeted therapy or assess therapeutic response. A biomarker is a biologic characteristic that is measured and evaluated objectively as an indicator of normal biologic processes, pathogenic processes, or pharmacologic response to therapeutic intervention (De Gruttola et al.: Considerations in the evaluation of surrogate endpoints in clinical trials. Summary of a National Institutes of Health workshop. *Control Clin Trials* 22: 485-502 (2001); Biomarkers and surrogate endpoints: Preferred definitions and conceptual framework. *Clin Pharmacol Ther* 69: 89-95 (2001). Biomarkers may be any parameter of a patient that can be measured, for example, mRNA expression profiles, proteins, proteomic patterns, lipids, imaging methods, or electrical signals.

In a broad embodiment of the invention, the biomarkers of the invention—LKB1 is used to predict a patient's sensitivity to a treatment protocol comprising an IGF-1R inhibitor. Particular embodiments of the invention disclosed herein include measuring polypeptide biomarker expression levels for patient selection. mRNA's corresponding to LKB1 or a fragment thereof are also included.

The present invention also features biomarker gene products, i.e., proteins and fragments thereof. The biomarker proteins of the invention include those specifically identified herein, as well as allelic variants, conservative substitution variants and homologs that can be isolated/generated and characterized without undue experimentation following the methods outlined herein. Fusion proteins that combine parts of different biomarker proteins or fragments thereof, as well as fusion proteins of a biomarker protein and a heterologous polypeptide are also included. Such biomarker proteins will be collectively referred to as biomarker proteins, marker proteins, or biomarker gene products.

In general, naturally occurring allelic variants of a biomarker protein of the invention will share a high degree of structural identity and homology (e.g., 90% or more identity). Typically, allelic variants of the biomarker protein will contain conservative amino acid substitutions within a biomarker protein sequences described herein or will contain a substitution of an amino acid from a corresponding position in a biomarker protein homologue. One class of biomarker protein allelic variants will be proteins that share a high degree of homology with at least a small region of a particular biomarker protein amino acid sequence, but will further contain a radical departure from the sequence, such as a non-conservative substitution, truncation, insertion or frame shift.

Conservative amino acid substitutions can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

Embodiments of the invention disclosed herein include a wide variety of art accepted variants of proteins such as polypeptides having amino acid insertions, deletions and substitutions. Variants can be made using methods known in the art such as site-directed mutagenesis, alanine scanning, and PCR mutagenesis. Site-directed mutagenesis (Carter, et al. (1986) Nucl. Acids Res. 13:4331; Zoller, et al. (1987) Nucl. Acids Res. 10:6487), cassette mutagenesis (Wells, et al. (1985) Gene 34:315), restriction selection mutagenesis (Wells, et al. (1986) Philos. Trans. R. Soc. London Ser. A 317:415) or other known techniques can be performed on the cloned DNA to produce the variant DNA. Scanning ammo acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, The Proteins, (W.H. Freeman & Co., N.Y.); Chothia (1976) J. Mol. Biol. 150:1). If alanine substitution does not yield adequate amounts of variant, an isosteric amino acid can be used.

As defined herein, biomarker protein variants have the distinguishing attribute of having at least one epitope in common with the biomarker protein having an amino acid sequence disclosed in SEQ ID NO:1 such that an antibody that specifically binds to a biomarker protein variant will also specifically bind to the biomarker protein of the invention—LKB1. A polypeptide ceases to be a variant when it no longer contains an epitope capable of being recognized by an antibody that specifically binds to a biomarker protein. Those skilled in the art understand that antibodies that recognize proteins bind to epitopes of varying size, and a grouping of the order of about six amino acids, contiguous or not, is regarded as a typical number of amino acids in a minimal epitope. See e.g., Hebbes, et al. (1989) Mol. Immunol. 26(9):865-73; Schwartz, et al. (1985) J. Immunol. 135(4):2598-608. As there are approximately 20 amino acids that can be included at a given position within the minimal 6 amino acid epitope, an approximation of the odds of such an epitope occurring by chance are about 20$^6$ or about 1 in 64 million. Another specific class of biomarker protein variants shares 90% or more identity with an amino acid sequence disclosed herein relative to the LKB 1 protein biomarker. The antibody specific for LKBI used in the methods of the invention is designated (27D10) mAb CST #3050. It is a rabbit LKB I antibody. Further information may be found at www.cellsignal.com/pdf/3050.pdf.

Biomarker proteins of the invention have a number of different specific uses. As the biomarker proteins of the invention are associated with transformed cells, cells undergoing Contact Normalization, and malignant and metastatic cancers, these proteins can be used in methods for identifying patients likely to respond favorably to an IGF-1R targeted therapy using, for example, an IGF-1R inhibitor. Methods for assessing therapeutic efficacy for the IGF-1R inhibitor in patients previously identified as being sensitive to treatment with an IGF-1R targeted therapy includes various assays known to one skilled in the art. As well, one may assess the efficacy of such a treatment protocol relative to a patient identified as being sensitive to treatment with an IGF-1R targeted therapy by various means including measuring tumor volume or any other clinically acceptable method of assessing therapeutic efficacy of an IGF-1R inhibitor. One such method propose s measuring tumor size or quantifying the number of IGF-1R expressing cell in said sensitive patient post treatment with the IGF-1R inhibitor, wherein the number is expected to be lower compared to pre-dose levels. Exemplary assays can use agents, e.g., antibodies, targeting or binding a biomarker protein disclosed herein.

The present invention provides a method for treating cancer or for identifying patients whose cancer is likely to be responsive to an IGF-1R inhibitory agent. The method is useful, inter alia, for increasing the likelihood that administration of an IGF-1R inhibitory anti-cancer therapy to a patient will be efficacious. Towards this end, the inventors have discovered that expression levels of LKB1 correlate with treatment outcome with an IGF-1R targeted therapy in patients presenting with an IGF-1R mediated cellular proliferative disorders.

It is noteworthy that while Phosphorylated IGF-1R levels and levels of IGF2 expression (indicating the presence of an active IGF2-IGF-1R autocrine loop) in cancer tissue might represent examples of candidate predictors of response to IGF-1R targeting therapies, the use of LKB1 expression as a predictor of response to an IGF-1R targeting therapy has escaped appreciation or recognition by the prior art. See Pollak et al., IGF1 Receptor: A Target for Cancer Treatment, *Nat Rev Cancer.* 2004; 4(7).

The terms "IGF-1R", "Insulin-like Growth Factor Receptor-I" and "Insulin-like Growth Factor Receptor, type I" are well known in the art. Although IGF-1R may be from any organism, it is preferably from an animal, more preferably from a mammal (e.g., mouse, rat, rabbit, sheep or dog) and most preferably from a human. The nucleotide and amino acid sequence of a typical human IGF-1R precursor is available at Genbank, eg. Gene ID 3480 or NM000875. Cleavage of the precursor (e.g., between amino acids 710 and 711) produces an α-subunit and a β-subunit which associate to form a mature receptor.

The term "IGF-1R inhibitory agent" includes any substance that decreases the expression, ligand binding, kinase activity or any other biological activity of IGF-1R that will elicit a biological or medical response of a tissue, system, subject or patient that is being sought by the administrator (such as a researcher, doctor or veterinarian) which includes any measurable alleviation of the signs, symptoms and/or clinical indicia of cancer (e.g., tumor growth) and/or the prevention, slowing or halting of progression or metastasis of cancer to any degree.

In an embodiment of the invention, an IGF-1R inhibitory agent that can be administered to a patient in a method according to the invention is any isolated anti-insulin-like growth factor receptor-1 (IGF-1R) antibody or fragment thereof (e.g., monoclonal antibodies (e.g., fully human monoclonal antibodies), polyclonal antibodies, bispecific antibodies, Fab antibody fragments, F(ab).sub.2 antibody fragments, Fv antibody fragments (e.g., VH or VL), single chain Fv antibody fragments, dsFv antibody fragments, humanized antibodies, chimeric antibodies or anti-idiotypic antibodies) such as any of those disclosed in any of Burtrum et. al., Cancer Research 63:8912-8921 (2003); in French Patent Applications FR2834990, FR2834991 and FR2834900 and in PCT Application Publication Nos. WO 03/100008; WO 03/59951; WO 04/71529; WO 03/106621; WO 04/83248; WO 04/87756 and WO 02/53596.

An "immunoglobulin" is a tetrameric molecule. In a naturally-occurring immunoglobulin, each tetramer is composed of two identical pairs of polypeptide chains, each pair having one "light" (about 25 kDa) and one "heavy" chain (about 50 70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as .kappa. and .lamda. light chains. Heavy chains are classified as .mu., .DELTA., .gamma., .alpha., or .epsilon., and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

The term "antibody" is used herein in the broadest sense and covers fully assembled antibodies, antibody fragments which retain the ability to specifically bind to the antigen (e.g., Fab, F(ab')2, Fv, and other fragments), single chain antibodies, diabodies, antibody chimeras, hybrid antibodies, bispecific antibodies, humanized antibodies, and the like. The term "antibody" covers both polyclonal and monoclonal antibodies. As well, the term includes an intact immunoglobulin or to an antigen-binding portion thereof that competes with the intact antibody for specific binding. Antigen-binding portions may be produced by recombinant DNA techniques or by enzymatic or chemical cleavage of intact antibodies.

"Patient" as that term is used herein, refers to the recipient of treatment. Mammalian and non-mammalian patients are included. In a particular embodiment, the patient is a human.

The IGF-1R antibody for use in the proposed combination therapeutic is one that specifically binds insulin-like growth factor 1 receptor (IGF-1R). Exemplary anti-IGF-1R antibodies for use in the combination therapeutic and methods for of use thereof are described in U.S. Pat. No. 7,241,444 (the '444 patent), filed Dec. 16, 2003, as a Continuation-in-part application of PCT/FR03/00178, filed Jan. 20, 2003, the entire content of which is incorporated by reference herein in its entirety. See e.g., claim 1 of the '444 patent.

As used in the application, the preferred IGF-1R inhibitory agent or IGF-1R inhibitor or IGF-1R antagonist refers to a humanized IGF-1R antibody disclosed in the '444 patent. Likewise, the disclosure of Ser. No. 11/801,080 is also incorporated by reference herein in its entirety.

"h7C10" or "MK-0646" are used interchangeably to describe a humanized antibody that is characterized as binding IGF-1R as well as binding the IR/IGF-1 hybrid receptor. Such a antibody preferably includes the antibody described the '444 patent, wherein the antibody or an antigen binding fragment thereof comprises a light chain and/or a heavy chain in which the skeleton segments FR1 to FR4 of said light chain and/or heavy chain are respectively derived from skeleton segments FR1 to FR4 of human antibody light chain and/or heavy chain. The humanized antibody may comprise at least one light chain that comprises at least one or more complementary determining regions derived from a non-human source and having the amino acid sequence selected from the group consisting of SEQ ID NOs: 4, 5 or 6 and at least one heavy chain comprising at least one or more complementary determining regions having an amino acid sequence selected from the group consisting of SEQ ID NOs 4, 5 or 6. The light chain may comprise one or more of the amino acid sequences as set forth in one of SEQ ID NOs. 7 or 8, or a sequence having at least 80% identity after optimum alignment with the sequence SEQ ID Nos: 7 or 8. Likewise, the heavy chain comprises one or more amino acid sequences as set forth in one of SEQ ID No. 9, 10 or 11, or a sequence having at least 80% identity after optimum alignment with the sequence SEQ ID Nos 9, 10 or 11. In certain embodiments, the methods of treatment include administering an antibody that binds the same epitope on IGF-1R as that bound by MK-0646.

Nucleic acid molecule for expressing the recombinant antibodies (IGF-1R specific mAbs) are described in the '444 patent, the content of which is incorporated by reference herein in its entirety.

"Diagnosing" a disease as used in the application is intended to include, for example, diagnosing or detecting the presence of a pathological hyperproliferative oncogenic disorder associated with or mediated by expression of IGF-1R, monitoring the progression of the disease, and identifying or detecting cells or samples that are indicative of a disorder associated with expression of IGF-1R. The terms diagnosing, detecting, identifying etc. are used interchangeably herein.

"Pathology" as used herein—The "pathology" caused by cancer cells within a host is anything that compromises the well-being or normal physiology of the host. This may involve, but is not limited to abnormal or uncontrollable growth of the cancer cell, metastasis, increase in expression levels of IGF-1R bearing cells, or other products at an inappropriate level, manifestation of a function inappropriate for its physiological milieu, interference with the normal function of neighboring cells, aggravation or suppression of an inflammatory or immunological response, or the harboring of undesirable chemical agents or invasive organisms.

"Treatment" of an individual or a cell is any type of intervention in an attempt to alter the non-treated course of the individual or cell. For example, treatment of an individual may be undertaken to decrease or limit the pathology caused by a cancer harbored in the individual. Treatment includes but is not limited to a) administration of a composition or a combination therapeutic, such as a pharmaceutical composition comprising an IGF-1R specific mAb and a tyrosine kinase inhibitor. The term "treating" refers to having a therapeutic effect and at least partially alleviating or abrogating an abnormal condition in the organism. Treating includes inhibition of tumor growth, maintenance of inhibited tumor growth, and induction of remission.

As used herein, the term "about" refers to an approximation of a stated value within an acceptable range. Preferably the range is +/−5% of the stated value.

The term "or" is used herein to mean, and is used interchangeably with, the term "and/or", unless context clearly indicates otherwise.

For the purposes herein a "section" of a tissue sample is meant a single part or piece of a tissue sample, e.g. a thin slice of tissue or cells cut from a tissue sample. It is understood that multiple sections of tissue samples may be taken and subjected to analysis according to the present invention.

In a preferred embodiment of the invention, a tissue sample or specimen, such as urine, blood, or other readily obtainable and minimally invasive biological sample, is obtained from the patient. The sample is used to generate cell or specimen lysates. Any methodology, including the ones described herein below, may be used to make cell or specimen lysates.

The term "sensitivity" and "sensitive" when made in reference to treatment with an IGF-1R inhibitor is a relative term which refers to the degree of effectiveness of the IGF-1R inhibitor compound in lessening or decreasing the progress of a tumor or the disease being treated. For example, the term "increased sensitivity" when used in reference to treatment of a cell or tumor in connection with the IGF-1R inhibitor compound refers to an increase of, at least a 5%, or more, in the effectiveness of the tumor treatment.

As used herein, and unless otherwise specified, the term "therapeutically effective amount" of an IGF-1R inhibitor compound is an amount sufficient to provide a therapeutic benefit in the treatment or management of a cancer, or to delay or minimize one or more symptoms associated with the presence of the cancer. A therapeutically effective amount of a compound means an amount of therapeutic agent, alone or in combination with other therapies, which provides a therapeutic benefit in the treatment or management of the cancer. The term "therapeutically effective amount" can encompass an amount that improves overall therapy, reduces or avoids symptoms or causes of cancer, or enhances the therapeutic efficacy of another therapeutic agent. It also refers to any increase in the therapeutic benefit to the patient. It may, for example, be 5%, 10%, 25%, 50%, or 100% decrease in the rate of progress of the tumor or in the decrease in the physical symptoms of a cancer or an increase in the general health of the patient, as measured by any suitable means, such as gene expression, cell counts, assay results, etc.

The term "predict" generally means to determine or tell in advance. When used to "predict" the effectiveness of a cancer treatment, for example, the term "predict" can mean that the likelihood of the outcome of the cancer treatment can be determined at the outset, before the treatment has begun, or before the treatment period has progressed substantially.

An improvement in the cancer or cancer-related disease can be characterized as a complete or partial response. "Complete response" refers to an absence of clinically detectable disease with normalization of any previously abnormal radiographic studies, bone marrow, and cerebrospinal fluid (CSF) or abnormal monoclonal protein measurements. "Partial response" refers to at least about a 10%, 20%, 30%, 40%, 50%, 60%, 70%, 80%, or 90% decrease in all measurable tumor burden (i.e., the number of malignant cells present in the subject, or the measured bulk of tumor masses or the quantity of abnormal monoclonal protein) in the absence of new lesions. The term "treatment" contemplates both a complete and a partial response.

"Tumor," as used herein, refers to all neoplastic cell growth and proliferation, whether malignant or benign, and all pre-cancerous and cancerous cells and tissues.

"Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth.

A feature of cancer cells is the tendency to grow in a manner that is uncontrollable by the host, but the pathology associated with a particular cancer cell may take any form. Primary cancer cells (that is, cells obtained from near the site of malignant transformation) can be readily distinguished from non-cancerous cells by well-established pathology techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. "Cancer" or "malignancy" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. A "cancerous" or "malignant cell" is understood as a cell having specific structural properties, lacking differentiation and being capable of invasion and metastasis. Examples of cancers are kidney, colon, breast, prostate and liver cancer. (see DeVita, V. et al. (eds.), 2001, Cancer Principles And Practice Of Oncology, 6.sup.th Ed., Lippincott Williams & Wilkins, Philadelphia, Pa.; this reference is herein incorporated by reference in its entirety for all purposes). While the examples detail predicting sensitivity to an IGF-1R inhibitor in the treatment of NSCLC, the term "cancer" is not so limited. It includes any and all tumours that are IGF-1R dependent as well as EOFR-dependent. Exemplary cancers if this type includes for example pancreatic cancer, breast cancer, colon cancer, prostate cancer, Rhabdomyosarcoma Ewing's sarcoma, and other pediatric cellular proliferative disorders. The term also includes cancer "responsive" to treatment with an IGF-1R inhibitor and any other cancer or proliferative disease, condition, trait, genotype or phenotype that can respond to the modulation of disease related gene expression in a cell or tissue, alone or in combination with other therapies.

As used herein the terms "polypeptide" and "protein" as used interchangeably herein, refer to a polymer of amino acids of three or more amino acids in a serial array, linked through peptide bonds. The term "polypeptide" includes proteins, protein fragments, protein analogues, oligopeptides and the like. The term polypeptide as used herein can also refer to a peptide. The amino acids making up the polypeptide may be naturally derived, or may be synthetic. The polypeptide can be purified from a biological sample.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from the RNA molecule to a protein, a polypeptide or a portion thereof.

An mRNA that is "upregulated" is generally increased upon a given treatment or condition. An mRNA that is "downregulated" generally refers to a decrease in the level of expression of the mRNA in response to a given treatment or condition. In some situations, the mRNA level can remain unchanged upon a given treatment or condition.

An mRNA from a patient sample can be "upregulated" when treated with an IGF-1R inhibitor, as compared to a non-treated control. This upregulation can be, for example, an increase of about 5%, 10%, 20%, 30%, 40%, 50%, 60%, 70%, 90%, 1000%, 200%, 300%, 500%, 1,000%, 5,000% or more of the comparative control mRNA level. Alternatively, an mRNA can be "downregulated", or expressed at a lower level, in response to administration of certain IGF-1R inhibitors or other agents. A downregulated mRNA can be, for example, present at a level of about 99%, 95%, 90%, 80%, 70%, 60%, 50%, 40%, 30%, 20%, 10%, 1% or less of the comparative control mRNA level.

Similarly, the expression level of a polypeptide or protein biomarker in a sample is decreased relative to a control. This decrease can be about 5%, 10%, 20%, 30%, 40%, 50%, 60%, 70%, 90%, 100%, 200%, 300%, 500%, 1,000%, 5,000% or more of the comparative control protein level or it may be expressed as a two or three fold difference or decrease in expression.

The terms "determining", "measuring", "evaluating", "assessing" and "assaying" as used herein generally refer to any form of measurement, and include determining if an element is present or not. These terms include both quantitative and/or qualitative determinations. Assessing may be relative or absolute. "Assessing the presence of" can include determining the amount of something present, as well as determining whether it is present or absent.

The terms "nucleic acid" and "polynucleotide" are used interchangeably herein to describe a polymer of any length composed of nucleotides, e.g., deoxyribonucleotides or ribonucleotides, or compounds produced synthetically, which can hybridize with naturally occurring nucleic acids in a sequence specific manner analogous to that of two naturally occurring nucleic acids, e.g., can participate in Watson-Crick base pairing interactions. As used herein in the context of a polynucleotide sequence, the term "bases" (or "base") is synonymous with "nucleotides" (or "nucleotide"), i.e. the monomer subunit of a polynucleotide. The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. "Analogues" refer to molecules having structural features that are recognized in the literature as being mimetics, derivatives, having analogous structures, or other like terms, and include, for example, polynucleotides incorporating non-natural nucleotides, nucleotide mimetics such as 2'-modified nucleosides, peptide nucleic acids, oligomeric nucleoside phosphonates, and any polynucleotide that has added substituent groups, such as protecting groups or linking moieties.

The term "complementary" refers to specific binding between polynucleotides based on the sequences of the polynucleotides. As used herein, a first polynucleotide and a second polynucleotide are complementary if they bind to each other in a hybridization assay under stringent conditions, e.g. if they produce a given or detectable level of signal in a hybridization assay. Portions of polynucleotides are complementary to each other if they follow conventional base-pairing rules, e.g. A pairs with T (or U) and G pairs with C, although small regions (e.g. less than about 3 bases) of mismatch, insertion, or deleted sequence may be present.

"Sequence identity" or "identity" in the context of two nucleic acid sequences refers to the residues in the two sequences which are the same when aligned for maximum correspondence over a specified comparison window, and can take into consideration additions, deletions and substitutions.

The term "substantial identity" or "homologous" in their various grammatical forms in the context of polynucleotides generally means that a polynucleotide comprises a sequence that has a desired identity, for example, at least 60% identity, preferably at least 70% sequence identity, more preferably at least 80%, still more preferably at least 90% and even more preferably at least 95%, compared to a reference sequence.

Another indication that nucleotide sequences are substantially identical is if two molecules hybridize to each other under stringent conditions.

As used herein, the term "bound" can be used herein to indicate direct or indirect attachment. In the context of chemical structures, "bound" (or "bonded") may refer to the existence of a chemical bond directly joining two moieties or indirectly joining two moieties (e.g. via a linking group or any other intervening portion of the molecule). The chemical bond may be a covalent bond, an ionic bond, a coordination complex, hydrogen bonding, van der Waals interactions, or hydrophobic stacking, or may exhibit characteristics of multiple types of chemical bonds. In certain instances, "bound" includes embodiments where the attachment is direct and also embodiments where the attachment is indirect.

The terms "isolated" and "purified" refer to isolation of a substance (such as mRNA or protein) such that the substance comprises a substantial portion of the sample in which it resides, i.e. greater than the substance is typically found in its natural or un-isolated state. Typically, a substantial portion of the sample comprises, e.g., greater than 1%, greater than 2%, greater than 5%, greater than 10%, greater than 20%, greater than 50%, or more, usually up to about 90%-100% of the sample. For example, a sample of isolated mRNA can typically comprise at least about 1% total mRNA. Techniques for purifying polynucleotides are well known in the art and include, for example, gel electrophoresis, ion-exchange chromatography, affinity chromatography, flow sorting, and sedimentation according to density.

The term "sample" as used herein relates to a material or mixture of materials, typically, although not necessarily, in fluid form, containing one or more components of interest.

"Biological sample" as used herein refers to a sample obtained from a biological subject, including sample of biological tissue or fluid origin, obtained, reached, or collected in vivo or in situ. A biological sample also includes samples from a region of a biological subject containing precancerous or cancer cells or tissues. Such samples can be, but are not limited to, organs, tissues, fractions and cells isolated from a mammal. Exemplary biological samples include but are not limited to cell lysate, a cell culture, a cell line, a tissue, oral tissue, gastrointestinal tissue, an organ, an organelle, a biological fluid, a blood sample, a urine sample, a skin sample, and the like. Preferred biological samples include but are not limited to whole blood, partially purified blood, PBMCs, tissue biopsies, and the like.

A "label" or a "detectable moiety" in reference to a nucleic acid, refers to a composition that, when linked with a nucleic acid, renders the nucleic acid detectable, for example, by spectroscopic, photochemical, biochemical, immunochemical, or chemical means. Exemplary labels include, but are not limited to, radioactive isotopes, magnetic beads, metallic beads, colloidal particles, fluorescent dyes, enzymes, biotin, digoxigenin, haptens, and the like. A "labeled nucleic acid or oligonucleotide probe" is generally one that is bound, either covalently, through a linker or a chemical bond, or noncovalently, through ionic bonds, van der Waals forces, electrostatic attractions, hydrophobic interactions, or hydrogen bonds, to a label such that the presence of the nucleic acid or probe can be detected by detecting the presence of the label bound to the nucleic acid or probe.

The term "status" in the context of the present invention is used in its art accepted meaning and refers to the condition or state of a gene or its products. As specifically described herein, the status of a biomarker can be evaluated by a number of parameters known in the art. Typically an alteration in the status of a biomarker includes a decrease or increase in biomarker mRNA and/or protein expression.

Biomarker proteins can be embodied in many forms, preferably in isolated form. As used herein, a protein is said to be "isolated" when physical, mechanical or chemical methods are employed to remove the biomarker protein from cellular constituents that are normally associated with the protein. A skilled artisan can readily employ standard purification methods to obtain an isolated biomarker protein. A purified biomarker protein molecule will be substantially free of other proteins or molecules that impair the binding of biomarker to antibody or other ligand. The nature and degree of isolation and purification will depend on the intended use.

Biomarker proteins, e.g., LKB1 can be generated using standard peptide synthesis technology or using chemical cleavage methods well-known in the art based on the amino acid sequences of the biomarker proteins disclosed herein. Alternatively, recombinant methods can be used to generate polynucleotides that encode a biomarker protein. In this regard, the biomarker-encoding polynucleotides described herein provide means for generating full-length and defined fragments of biomarker proteins.

The biomarker proteins of the present invention can also be modified in a way to form a chimeric molecule containing a biomarker protein fused to another, heterologous polypeptide or amino acid sequence. In one embodiment, such a chimeric molecule is a fusion of the biomarker protein with a polyhistidine epitope tag, which provides an epitope to which immobilized nickel can selectively bind. The epitope tag is generally placed at the amino- or carboxyl-terminus of the biomarker protein. In an alternative embodiment, the chimeric molecule can include a fusion of the biomarker protein with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a biomarker protein in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130.

The invention also provides various immunological assays useful for the binding to, detection and quantification of the biomarker protein disclosed herein. Such methods and assays generally include one or more biomarker-specific antibodies capable of recognizing and binding a biomarker protein, as appropriate, and can be performed within various immunological assay formats well-known in the art, including but not limited to various types of radioimmunoassays, enzyme-linked immunosorbent assays (ELISA), enzyme-linked immunofluorescent assays (ELIFA), and the like. In addition, immunological imaging methods capable of detecting cancers expressing biomarker proteins are also provided by the invention, including but not limited to radioscintigraphic imaging methods using labeled biomarker protein-specific antibodies. Such assays may be clinically useful in the detection, monitoring, and prognosis of cancers such as prostate, breast, pancreas, colon and ovarian cancers. Antibodies may also be used in methods for purifying biomarker proteins and for isolating biomarker protein homologues and related molecules.

Various methods for the preparation of antibodies are well-known in the art. For example, antibodies may be prepared by immunizing a suitable mammalian host using a biomarker protein, peptide, or fragment, in isolated or immunoconjugated form (Harlow & Lane, eds. (1988) Antibodies: A Laboratory Manual, CSH Press). In addition, fusion proteins can also be used, such as a biomarker protein GST-fusion. In other embodiments, a biomarker peptide may be synthesized and used as an immunogen.

In addition, naked DNA immunization techniques known in the art can be used (with or without purified biomarker protein or biomarker protein expressing cells) to generate an immune response to the encoded immunogen (for review, see Donnelly, et al. (1997) Ann. Rev. Immunol. 15:617-648).

Methods for preparing a protein or peptide for use as an immunogen and for preparing immunogenic conjugates of a protein with a carrier such as BSA, KLH, or other carrier proteins are well-known in the art. In some circumstances, direct conjugation using, for example, carbodimide reagents can be used; in other instances linking reagents such as those supplied by Pierce Chemical Co., Rockford, Ill., may be effective. Administration of a biomarker protein immunogen is conducted generally by injection over a suitable time period and with use of a suitable adjuvant, as is generally understood in the art. During the immunization schedule, titers of antibodies can be taken to determine adequacy of antibody formation.

Monoclonal antibodies are preferred and may be produced by various means well-known in the art. For example, immortalized cell lines that secrete a desired monoclonal antibody can be prepared using the standard hybridoma technology of Kohler and Milstein or modifications that immortalize producing B cells, as is generally known. The immortalized cell lines secreting the desired antibodies are screened by immunoassay in which the antigen is the biomarker protein or protein fragment. When the appropriate immortalized cell culture secreting the desired antibody is identified, the cells may be expanded and antibodies produced either from in vitro cultures or from ascites fluid. A representative method of generating the humanized antibody of the invention is disclosed in U.S. Pat. No. 7,244,444, the content of which is incorporated by reference in its entirety. See, for example, Examples 1-4 of said patent.

Antibodies or fragments including those that bind LKB1 and IGF-1R can also be produced by recombinant means. Regions that bind specifically to the desired regions of the biomarker protein can also be produced in the context of chimeric or CDR grafted antibodies of multiple species origin. Humanized or human antibodies can also be produced and are preferred for use in therapeutic contexts. Methods for humanizing murine and other non-human antibodies by substituting one or more of the non-human antibody CDRs for corresponding human antibody sequences are well-known (see, for example, Jones, et al. (1986) Nature 321:522-525; Riechmann, et al. (1988) Nature 332:323-327; Verhoeyen, et al. (1988) Science 239:1534-1536). Methods for producing fully human monoclonal antibodies include phage display and transgenic methods (for review, see Vaughan, et al. (1998) Nature Biotechnology 16:535-539).

Fully human monoclonal antibodies can be generated using cloning technologies employing large human Ig gene combinatorial libraries (i.e., phage display). Fully human monoclonal antibodies can also be produced using transgenic mice engineered to contain human immunoglobulin gene loci as described in WO 98/24893. This method avoids the in vitro manipulation required with phage display technology and efficiently produces high affinity authentic human antibodies.

Reactivity or binding of antibodies with a biomarker protein e.g., LKB1 can be established by a number of well-known means, including western blot, immunoprecipitation, ELISA, and FACS analyses using, as appropriate, biomarker proteins, peptides, or cell extracts.

An antibody or fragment thereof that bind the biomarker protein of the invention can be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. A second molecule for conjugation to the antibody can be selected in accordance with the intended use. For example, for therapeutic use, the second molecule can be a toxin or therapeutic agent.

Further, bi-specific antibodies specific for two or more epitopes may be generated using methods generally known in the art. Homodimeric antibodies may also be generated by cross-linking techniques known in the art (e.g., Wolff, et al. (1993) Cancer Res. 53:2560-2565).

Polynucleotides encoding the protein biomarker of the present invention can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA that is integrated into the genome of a cell from which a transgenic animal develops. In one embodiment, cDNA encoding a biomarker of the invention can be used to clone genomic DNA encoding the biomarker in accordance with established techniques and the genomic sequences used to generate transgenic animals that contain cells that express DNA encoding the biomarker. Methods for generating transgenic animals, particularly animals such as mice or rats, have become conventional in the art and are described, for example, in U.S. Pat. Nos. 4,736,866 and 4,870,009. Typically, particular cells would be targeted for transgene incorporation with tissue-specific enhancers. Transgenic animals that include a copy of a transgene encoding the biomarker introduced into the germ line of the animal at an embryonic stage can be used to examine the effect of increased expression of DNA encoding the biomarker. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, the biomarker of the invention can be used to construct a "knock out" animal that has a defective or altered gene encoding the biomarker as a result of homologous recombination between the endogenous gene encoding the biomarker and altered genomic DNA encoding the biomarker introduced into an embryonic cell of the animal. For example, cDNA encoding a biomarker can be used to clone genomic DNA encoding the biomarker in accordance with established techniques. A portion of the genomic DNA encoding the biomarker can be deleted or replaced with another gene, such as a gene encoding a selectable biomarker that can be used to monitor integration. Typically, several kilobases of unaltered flanking DNA (both at the 5' and 3' ends) are included in the vector (see e.g., Thomas & Capecchi (1987) Cell 51:503) for a description of homologous recombination vectors). The vector is introduced into an embryonic stem cell line (e.g., by electroporation) and cells in which the introduced DNA has homologously recombined with the endogenous DNA are selected (see e.g., Li, et al. (1992) Cell 69:915). The selected cells are then injected into a blastocyst of an animal (e.g., a mouse or rat) to form aggregation chimeras (see e.g., Bradley, in Robertson, ed. (1987) Teratocarcinomas and Embryonic Stem Cells: A Practical Approach, (IRL, Oxford), pp. 113-152). A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the biomarker protein.

The present invention in addition to providing methods for detecting biomarker protein expression levels also provides methods for detecting biomarker genes as well as methods for identifying a cell that aberrantly expresses the biomarker, e.g. decreased expression relative to a control cell. The analysis disclosed herein indicates that the biomarker of the present invention is aberrantly expressed (decreased expression) in transformed cells or cells affected by contact normalization. In this context, the status of biomarker gene product can provide information useful for predicting a variety of factors including susceptibility to treatment with an IGF-1R inhibitor compound, e.g. sensitivity or resistance to treatment and/or patient selection (stratification). The status of biomarker gene and gene products in patient samples can be analyzed by a variety protocols that are well-known in the art including immunohistochemical analysis, the variety of northern blotting techniques including in situ hybridization, RT-PCR analysis (for example on laser capture micro-dissected samples), western blot analysis and tissue array analysis using agents disclosed herein that bind biomarker genes and gene products.

The term "absolute amplitude" of correlation expressions means the distance, either positive or negative, from a zero value; i.e., both correlation coefficients −0.35 and 0.35 have an absolute amplitude of 0.35.

As used herein, "subject" refers to an organism or to a cell sample, tissue sample or organ sample derived therefrom, including, for example, cultured cell lines, biopsy, blood sample or fluid sample containing a cell. In many instances, the subject or sample derived therefrom, comprises a plurality of cell types. In one embodiment, the sample includes, for example, a mixture of tumor cells and normal cells. In one embodiment, the sample comprises at least 10%, 15%, 20%, et seq., 90%, or 95% tumor cells. In one embodiment, the organism is a mammal, such as a human, canine, murine, feline, bovine, ovine, swine or caprine. In a particular embodiment, the organism is a human patient.

As used herein, the terms "combination treatment", "combination therapy", "combined treatment" or "combinatorial treatment", used interchangeably, refer to a treatment of an individual with at least two different therapeutic agents. According to the invention, the individual is treated with a first therapeutic agent, preferably the anti-IGF-1R antibody as described in the '444 patent. The second therapeutic agent may be another IGF-1R pathway inhibitor or may be any clinically established anti-cancer agent such as for example, a tyrosine kinase inhibitor, a VEGF inhibitor, an mTOR inhibitor or an AKT inhibitor. A combinatorial treatment may include a third or even further therapeutic agent.

As used herein, the terms "measuring expression levels," "obtaining an expression level" and the like, includes methods that quantify a gene expression level of, for example, a transcript of a gene, including microRNA (miRNA) or a protein encoded by a gene, as well as methods that determine whether a gene of interest is expressed at all. Thus, an assay which provides a "yes" or "no" result without necessarily providing quantification of an amount of expression is an assay that "measures expression" as that term is used herein. Alternatively, a measured or obtained expression level may be expressed as any quantitative value, for example, a fold-change in expression, up or down, relative to a control gene or relative to the same gene in another sample, or a log ratio of expression, or any visual representation thereof, such as, for example, a "heatmap" where a color intensity is representative of the amount of gene expression detected. Exemplary methods for detecting the level of expression of a gene include, but are not limited to, Northern blotting, dot or slot blots, reporter gene matrix (see, for example, U.S. Pat. No. 5,569,588), nuclease protection, RT-PCR, microarray profiling, differential display, SAGE (Velculescu et al., 1995, Science 270:484-87), Digital Gene Expression System (see WO2007076128; WO2007076129), multiplex mRNA assay (Tian et al., 2004 Nucleic Acids Res. 32:e126), PMAGE (Kim et al., 2007 Science 316:1481-84), cDNA-mediated annealing, selection, extension and ligation assay (DASL, Bibikova, et al., 2004, AJP 165:1799-807), multiplex branched DNA assay (Flagella et al., 2006, Anal. Biochem. 352:50-60), 2D gel electrophoresis, SELDI-TOF, ICAT, enzyme assay, antibody assay, and the like.

"Differential Result" as used herein is generally obtained from an assay in which a comparison is made between the findings of two different assay samples, such as a cancerous cell line and a control cell line or a cancerous tissue and a control tissue. Thus, for example, "differential levels" of a marker protein, such as LKB1 are observed when the level of LKB1 is lower in one sample than another.

The level of LKB1 expression is advantageously compared or measured in relation to levels in a control cell or sample also referred to as a "reference level". "Reference level" and "control" are used interchangeably in the specification. Broadly speaking, a "control level" means a separate baseline level measured in a comparable control cell, which is generally disease free. It may be from the same individual or from another individual who is normal or does not present with the same disease from which the diseased or test sample is obtained. Within the context of the present invention, the term "reference level" refers to a "control level" of expression of LKB1 used to evaluate a test level of expression of LKB1 in a cancer cell-containing sample of a patient. For example, when the level of LKB1 in the biological sample of a patient is lower than the reference level of LKB1, the cells will be considered to have a low or decreased level of expression, or underexpression of LKB1. The reference level can be determined by a plurality of methods, provided that the resulting reference level accurately provides a level of LKB1 below which exists a first group of patients having a different probability of sensitivity to treatment with an IGF-1R inhibitor than that of a second group of patients having levels of the LKB1 above the reference level-resistant to treatment with an IGF-1R inhibitor. Expression levels may thus define IGF-1R bearing cells or alternatively the level of expression of IGF-1R independent of the number of cells expressing IGF-1R Thus the reference level for each patient can be proscribed by a reference ratio of LKB1, wherein the reference ratio can be determined by any of the methods for determining the reference levels described herein. For example, the control maybe a predetermined value, which can take a variety of forms. It can be a single cut-off value, such as a median or mean. The "reference level" can be a single number, equally applicable to every patient individually, or the reference level can vary, according to specific subpopulations of patients. Thus, for example, older men might have a different reference level than younger men for the same cancer, and women might have a different reference level than men for the same cancer. Alternatively, the "reference level" can be determined by measuring the level of expression of LKB1 in non-tumorous cancer cells from the same tissue as the tissue of the neoplastic cells to be tested. As well, the "reference level" might be a certain ratio of LKB1 in the neoplastic cells of a patient relative to the LKB1 levels in non-tumor cells within the same patient. The "reference level" can also be a level of LKB1 of in vitro cultured cells, which can be manipulated to simulate tumor cells, or can be manipulated in any other manner which yields expression levels which accurately determine the reference level. On the other hand, the "reference level" can be established based upon comparative groups, such as in groups not having elevated LKB1 levels and groups having elevated LKB1 levels. Another example of comparative groups would be groups having a particular disease, condition or symptoms and groups without the disease. Thus, for example, when looking to establish a "reference level" for colon cancer presenting patients, the comparative group may comprise patients presenting with colon cancer and those that do not. Another comparative group would be a group with a family history of a condition, e.g., breast cancer and a group without such a family history. The predetermined value can be arranged, for example, where a tested population is divided equally (or unequally) into groups, such as a low-risk group, a medium-risk group and a high-risk group or into quandrants or quintiles, the lowest quandrant or quintile being individuals with the lowest risk or lowest amount of LKB1 and the highest quandrant or quintile being individuals with the highest risk or highest amount of LKB1.

The reference level can also be determined by comparison of the level of LKB1 in populations of patients having the same cancer. This can be accomplished, for example, by histogram analysis, in which an entire cohort of patients are graphically presented, wherein a first axis represents the level of LKB1, and a second axis represents the number of patients in the cohort whose neoplastic cells express LKB1 at a given level. Two or more separate groups of patients can be determined by identification of subsets populations of the cohort which have the same or similar levels of LKB1. Determination of the reference level can then be made based on a level which best distinguishes these separate groups. A reference level also can represent the levels of two or more markers, one of which is LKB1. Two or more markers can be represented, for example, by a ratio of values for levels of each marker.

Likewise, an apparently healthy population will have a different 'normal' range than will a population which is known to have a condition associated with expression of LKB1 such as for example, colon cancer. Accordingly, the predetermined value selected may take into account the category in which an individual falls. Appropriate ranges and categories can be selected with no more than routine experimentation by those of ordinary skill in the art. By "decreased" it is meant low relative to a selected control. Typically the control will be based on apparently healthy normal individuals in an appropriate age bracket.

It will also be understood that the controls according to the invention may be, in addition to predetermined values, samples of materials tested in parallel with the experimental materials. Examples include tissue or cells obtained at the same time from the same subject, for example, parts of a single biopsy, or parts of a single cell sample from the subject.

Thus, in one aspect, the LKB1 specific reagents such as LKB1 specific antibodies detailed herein or binding fragments thereof will be very useful in prognosis of cancer treatment outcome by effectively allowing one skilled in the art to quantitate or quantify the expression levels of LKB1 in whatever kind of "sample" it may occur, such samples including tissue samples such as biopsied tissues, fluid, or semi-fluid samples.

For quantifying the level of LKB1 expression, one skilled in the art may combine and/or competitively react antibodies of the invention or fragments thereof, a test fluid and a labeled form of LKB1, measure a ratio of the labeled LKB1 bound to the antibodies or fragments thereof b to thereby quantify the LKB1 in the test fluid.

II. Aspects and Embodiments of the Invention

In a broad aspect, the invention provides methods for identifying patients likely to be sensitive to treatment with an IGF-1R inhibitor. Methods of identifying patients likely to respond favorably to an IGF-1R targeted therapy are also included as are methods of treating patients so identified with an IGF-1R inhibitor. Assays for prognosing cancer treatment outcome in a IGF-1R targeted therapy are also provided which proposes detecting quantity of a wild type biomarker gene polynucleotides or its encoded gene product in a biological sample, wherein an decrease in the presence of the biomarker protein relative to a control cell predicts the sensitivity of the cells to treatment with an IGF-1R targeted therapy. In an alternative embodiment, the invention provides for the detection of presence of a loss of function protein in a biological sample, wherein presence of the loss of function protein is predictive of the sensitivity of the cells in the biological sample to treatment with an IGF-1R targeted therapy. Biological samples can be obtained from any mammalian source including human. Detectable biomarker polynucleotides include, for example, mRNA, and recombinant DNA or RNA molecules containing a biomarker polynucleotide. Detectable biomarker polypeptide include, for example expression of the encoded gene product—protein expression via well known methods including western blot etc. A number of methods for amplifying and/or detecting the presence or quantity of polynucleotides and polypeptides are well-known in the art and may be employed in the practice of this aspect of the invention.

In one embodiment, a method for detecting a biomarker gene mRNA in a biological sample includes obtaining a sample, producing cDNA from the sample by reverse transcription using at least one primer that binds the biomarker polynucleotide; amplifying the cDNA so produced using biomarker oligonucleotides as sense and antisense primers to amplifying cDNAs therein; and detecting the presence of the amplified cDNA. Such assays can be qualitative or quantitative. Any number of appropriate sense and antisense probe combinations may be designed from the polynucleotide(s) encoding the LKB1 biomarker protein. Single nucleotide polymorphisms (SNP's) and alternatively spliced variants of the target polynucleotide are also included.

The invention also provides assays for prognosing cancer treatment outcome by detecting the presence of a loss of function LKB1 protein or quantity (decreased expression level relative to a control cell) of the biomarker protein (LKB1) in a biological sample such as biopsy sample or other tissues and the like. Methods for detecting a biomarker protein are also well-known and include, for example, immunoprecipitation, immunohistochemical analysis, western blot analysis, molecular binding assays, ELISA, ELIFA and the like. For example, in one embodiment, a method of detecting the presence of the biomarker protein e.g., LKB1 in a biological sample includes obtaining a sample from a subject, contacting the sample with an agent that binds the biomarker protein, e.g., a biomarker-specific antibody and then determining the binding of the agent to the biomarker protein in the sample, wherein the presence of binding is indicative of the presence or expression level of the biomarker protein in the sample and hence cancer. Such assays can be qualitative or quantitative. The antibody may be any antibody specific for either the total amount of LKB1 protein in the sample or an antibody that detects the presence of a phosphorylated form of LKB1.

It is understood that in the methods of the invention detection of LKB1 or measurement for LKB1 expression may be accomplished via use of any LKB1 specific antibody—polyclonal or monoclonal, and from any source. Such detection may comprises detecting total LKB1 protein expression or may alternatively comprise measuring LKB1 expression levels by detecting phosphorylated LKB1 or its functional phosphorylated variant that is specific for LKB1 or a functionally equivalent thereof.

In addition to measuring decreased expression levels of wild type LKB1 in a patient sample relative to a to a control or normal cell as being predictive of sensitivity to treatment with an IGF-1R targeted therapy, e.g., IGF-1R inhibitor, the invention further provides for predicting sensitivity of an IGF-1R expressing tumor cell to an IGF-1R targeted therapy by measuring expression levels of a loss of function mutant LKB1 protein with or without increased IGR-1R expression in the same cell. Thus, in one embodiment, the invention provides measuring expression levels of a loss of function LKB1 protein biomarker and predicting the patient's sensitivity to treatment with an IGF-1R inhibitor based upon the expression level of said loss of function protein. In an alternative embodiment, the method further comprises measuring expression levels of IGF-1R in the same sample of cells wherein an increase in expression level of IGF-1R relative to a control cell is predictive of the patient's sensitivity or resistance to treatment with an IGF-1R inhibitor. A variety of other LKB11 gene mutations have been associated with the formation of sporadic cancers in several tissues. A list of mutants within LKB1 that are representative of a loss of function LKB1 protein for use in the methods of the invention are listed in Alessi et al, Annual Rev. Biochem.; 75:137-163 (2006) the content of which is incorporated by reference herein in its entirety. See FIG. 1, for example. It is understood that loss of function mutants in addition to those listed in Alessi et al., supra are also included.

Methods for identifying a cell that aberrantly expresses a biomarker protein are also provided. A cell that aberrantly expresses a biomarker e.g., LKB1 is intended to mean a cell exhibiting a reduced or an increased level of expression of the biomarker as compared to a control. As disclosed herein, such a comparison can be between transformed and nontransformed cells.

In one embodiment, an assay for identifying a cell that aberrantly expresses a biomarker gene includes detecting the presence or quantity of the biomarker mRNA e.g., LKB1 or functional equivalent thereof in the cell. Methods for the detection of particular mRNAs in cells are well-known and include, for example, hybridization assays using complementary DNA probes (such as in situ hybridization using labeled riboprobes, northern blot and related techniques) and various nucleic acid amplification assays (such as RT-PCR using complementary primers specific for the biomarker, and other amplification type detection methods, such as, for example, branched DNA, SISBA, TMA and the like). Alternatively, an assay for identifying a cell that aberrantly expresses a biomarker gene includes detecting the presence or quantity of a biomarker protein in the cell or secreted by the cell. Various methods for the detection of proteins are well-known in the art and may be employed for the detection of biomarker proteins and biomarker expressing cells.

The expression profile of the biomarker protein also makes it a potential diagnostic biomarker for local and/or metastasized disease. In particular, the status of a biomarker presence or expression level may provide information useful for predicting susceptibility to treatment outcome with say an IGF-1R inhibitor e.g., monotherapy or a combination therapy or disease stage progression, and/or tumor aggressiveness. The invention methods and assays may also find use in determining biomarker status and prognosing sensitivity of cancer cell types, such as cancers of the prostate, bladder, ovaries, testes, breast, pancreas, colon and lung. Biomarker status in patient samples can be analyzed by a number of means well-known in the art, including without limitation, immunohistochemical analysis, in situ hybridization, RT-PCR analysis on laser capture micro-dissected samples, western blot analysis of clinical samples and cell lines, and tissue array analysis.

Biomarker expression analysis may also be useful as a tool for identifying and evaluating agents that modulate biomarker gene expression. For example, cancers biomarkers with a decreased level of expression in a cancer cell can be used in the identification of a molecule or biological agent that could inhibit biomarker expression or over-expression in cancer cells. Such an agent may be identified by using a screen that quantifies biomarker expression by RT-PCR, nucleic acid hybridization or antibody binding to the gene product.

The biomarker protein sequences disclosed herein also allow the skilled artisan to identify proteins, antibodies, small molecules and other agents that interact with the biomarker via any one of a variety of art accepted protocols. These reagents may, in turn, be used to select patients likely to succeed (sensitive) or fail (resistant to) treatment with an IGF-1R targeted therapy. The IGF-1R targeted therapy may be a small molecule or an antibody and may comprise monotherapy with then IGF-1R inhibitor or a combination therapy wherein one arm may comprise a tyrosine kinase inhibitor.

The identification of the biomarkers disclosed herein opens a number of therapeutic approaches to the treatment of such cancers including malignant and metastatic cancers. Accordingly, therapeutic approaches aimed at identifying patient populations likely to be sensitive to treatment with an IGF-1R inhibitor are expected to be useful for patients with cancer or patients harboring cancer cells affected by aberrant growth or cellular proliferative disorders responsive to treatment with an IGF-1R inhibitor.

Antibodies (1) IGF-1R (h7C10)

As detailed herein, an aspect of the present invention is directed to a method of improving the anti-tumor efficacy of an anti-cancer agent by administering an IGF-1R targeted therapeutic to a patient previously selected as being sensitive to treatment with an IGF-1R inhibitor.

The preferred therapeutic antibody for practicing the invention is one that specifically binds insulin-like growth factor 1 receptor (IGF-1R). Exemplary anti-IGF-1R antibodies for use as the therapeutic antibody to IGF-1R sensitive cells is in described in the U.S. Pat. No. 7,241,444 ('444 patent) the content of which is incorporated by reference herein in its entirety. See for example Claim 1 of the '444 patent.

"h7C10" or "MK-0646" are used interchangeably to describe a humanized antibody that is characterized as binding IGF-1R as well as binding the IR/IGF-1 hybrid receptor. Such an antibody preferably includes the antibody described, for example, in the '444 patent, wherein the antibody is a humanized antibody or a fragment thereof and comprises a light chain and/or a heavy chain in which the skeleton segments FR1 to FR4 of said light chain and/or heavy chain are respectively derived from skeleton segments FR1 to FR4 of human antibody light chain and/or heavy chain. The humanized antibody may comprise at least one light chain that comprises at least one or more complementary determining regions derived from a non-human source and having the amino acid sequence selected from the group consisting of SEQ ID NOS: 3, 4 or 5 and at least one heavy chain comprising at least one or more complementary determining regions having an amino acid sequence selected from the group consisting of SEQ ID NOs 6, 7 or 8. The light chain may comprise one or more of the amino acid sequences as set forth in one of SEQ ID NOs. 9, 10 or 11, or a sequence having at least 80% identity after optimum alignment with the sequence SEQ ID Nos: 9, 10 or 11. Likewise, the heavy chain comprises one or more amino acid sequences as set forth in one of SEQ ID No. 12, 13, 14 or 15, or a sequence having at least 80% identity after optimum alignment with the sequence SEQ ID Nos 9, 10 or 11. In certain embodiments, the methods of treatment include administering an antibody that binds the same epitope on IGF-1R as that bound by MK-0646 or an antigen binding fragment thereof.

Nucleic acid molecule for expressing the recombinant antibodies (IGF-1R specific mAbs) are described in the '444 patent, the content of which is incorporated by reference herein in its entirety.

The antibodies for use in the present invention include, but are not limited to, monoclonal antibodies, synthetic antibodies, polyclonal antibodies, multispecific antibodies (including bi-specific antibodies), human antibodies, humanized antibodies, chimeric antibodies, single-chain Fvs (scfv) (including bi-specific scFvs), single chain antibodies, Fab fragments, F(ab') fragments, disulfide-linked Fvs (sdFv), and epitope-binding fragments of any of the above. In particular, antibodies for use in the present invention include immunoglobulin molecules and immunologically active portions of immunoglobulin molecules, i.e., molecules that contain a IGF-1R binding site that immunospecifically binds to IGF-1R. The immunoglobulin molecules for use in the invention can be of any type (e.g. IgG, IgE, IgM, IgD, IgA and IgY), class (e.g., IgG1, IgG2, IgG3, IgG4, IgA1 and IgA2) or subclass of immunoglobulin molecule. Preferably, the antibodies for use in the invention are IgG, more preferably, IgG.

The antibodies for use in the invention may be from any animal origin. Preferably, the antibodies are humanized monoclonal antibodies. Alternatively, the antibodies may be fully human so long as they bind the same epitope of the antibody claimed in the '444 patent. As used herein, "human" antibodies include antibodies having the amino acid sequence of a human immunoglobulin and include antibodies isolated from human immunoglobulin libraries or from mice or other animals that express antibodies from human genes.

The antibodies for use in the present invention may be monospecific, bispecific, trispecific or of greater multispecificity. Multispecific antibodies may immunospecifically bind to different epitopes of a polypeptide or may immunospecifically bind to both a polypeptide as well a heterologous epitope, such as a heterologous polypeptide or solid support material. See, e.g., International Publication Nos. WO 93/17715, WO 92/08802, WO 91/00360, and WO 92/05793; Tutt, et al., 1991, J. Immunol. 147:60-69; U.S. Pat. Nos. 4,474,893, 4,714,681, 4,925,648, 5,573,920, and 5,601,819; and Kostelny et al., 1992, J. Immunol. 148:1547-1553.

The antibodies for use in the invention include derivatives of the antibodies. Standard techniques known to those of skill in the art can be used to introduce mutations in the nucleotide sequence encoding an antibody to be used with the methods for use in the invention, including, for example, site-directed mutagenesis and PCR-mediated mutagenesis which result in amino acid substitutions. Preferably, the derivatives include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original molecule. In a preferred embodiment, the derivatives have conservative amino acid substitutions are made at one or more predicted non-essential amino acid residues. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed and the activity of the protein can be determined.

The antibodies for use in the present invention include derivatives that are modified, i.e., by the covalent attachment of any type of molecule to the antibody. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, synthesis in the presence of tunicamycin, etc. Additionally, the derivative may contain one or more non-classical amino acids.

The present invention also provides antibodies for use in the invention that comprise a framework region known to those of skill in the art. In certain embodiments, one or more framework regions, preferably, all of the framework regions, of an antibody to be used in the compositions and methods for use in the invention are human. In certain other embodiments for use in the invention, the fragment region of an antibody for use in the invention is humanized. In certain embodiments, the antibody to be used with the methods for use in the invention is a synthetic antibody, a monoclonal antibody, an intrabody, a chimeric antibody, a human antibody, a humanized chimeric antibody, a humanized antibody, a glycosylated antibody, a multispecific antibody, a human antibody, a single-chain antibody, or a bispecific antibody.

In certain embodiments, an antibody for use in the invention has a high binding affinity for IGF-1R.

In certain embodiments, an antibody for use in the present invention includes antigen-binding portions of an intact antibody that retain capacity to bind IGF-1R. Examples include (i) a Fab fragment, a monovalent fragment consisting of the VL, VH, CL and CH1 domains; (ii) a F(ab')2 fragment, ambivalent fragment comprising two Fab fragments linked by a disulfide bridge at the hinge region; (iii) a Fd fragment consisting of the VH and CH domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); See, e.g., Bird et al. (1988) Science 242:423-426; and Huston et al. (1988) Proc. Natl. Acad. Sci. USA 85:5879-5883). Such single chain antibodies are included by reference to the term "antibody."

Methods of producing antibodies to IGF-1R are well known. See for example, the '444 patent.

Screening for Antibody Specificity—Techniques for generating antibodies have been described above. One may further select antibodies with certain biological characteristics, as desired. Thus, once produced, the antibodies may be screened for their binding affinity for IGF-1R. Screening for antibodies that specifically bind to IGF-1R may be accomplished using an enzyme-linked immunosorbent assay (ELISA) in which microtiter plates are coated with IGF-1R. In some embodiments, antibodies that bind IGF-1R from positively reacting clones can be further screened for reactivity in an ELISA-based assay to other IGF-1R isoforms, for example, IGF-1R using microtiter plates coated with the other IGF-1R isoform(s). Clones that produce antibodies that are reactive to another isoform of IGF-1R are eliminated, and clones that produce antibodies that are reactive to IGF-1R only may be selected for further expansion and development. Confirmation of reactivity of the antibodies to IGF-1R may be accomplished, for example, using a Western Blot assay in which protein from ovarian, breast, renal, colorectal, lung, endometrial, or brain cancer cells and purified IGF-1R and other IGF-1R isoforms are run on an SDS-PAGE gel, and subsequently are blotted onto a membrane. The membrane may then be probed with the putative anti-IGF-1R antibodies. Reactivity with IGF-1R and not another insulin-like receptor isoform confirms specificity of reactivity for IGF-1R.

General methods for detecting IGF-1R or its Derivatives— The assaying method for detecting IGF-1R using the antibodies of the invention or binding fragments thereof are not particularly limited. Any assaying method can be used, so long as the amount of antibody, antigen or antibody-antigen complex corresponding to the amount of antigen (e.g., the level of IGF-1R) in a fluid to be tested can be detected by chemical or physical means and the amount of the antigen can be calculated from a standard curve prepared from standard solutions containing known amounts of the antigen. Representative immunoassays encompassed by the present invention include, but are not limited to, those described in U.S. Pat. No. 4,367,110 (double monoclonal antibody sandwich assay); Wide et al., Kirkham and Hunter, eds. Radioimmunoassay Methods, E. and S. Livingstone, Edinburgh (1970); U.S. Pat. No. 4,452,901 (western blot); Brown et al., J. Biol. Chem. 255: 4980-4983 (1980) (immunoprecipitation of labeled ligand); and Brooks et al., Clin. Exp. Immunol. 39:477 (1980) (immunocytochemistry); immunofluorescence techniques employing a fluorescently labeled antibody, coupled with light microscopic, flow cytometric, or fluorometric detection etc. See also Immunoassays for the 80's, A.

Voller et al., eds., University Park, 1981, Zola, Monoclonal Antibodies: A Manual of Techniques, pp. 147-158 (CRC Press, Inc. 1987).

(1) Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

In the sandwich assay, the immobilized antibody of the present invention is reacted with a test fluid (primary reaction), then with a labeled form of antibody of the present invention (secondary reaction), and the activity of the labeling agent on the immobilizing carrier is measured, whereby the IGF-1R level in the test fluid can be quantified. The primary and secondary reactions may be performed simultaneously or with some time intervals. The methods of labeling and immobilization can be performed by modifications of those methods described above. In the immunoassay by the sandwich assay, the antibody used for immobilized or labeled antibody is not necessarily from one species, but a mixture of two or more species of antibodies may be used to increase the measurement sensitivity, etc. In the method of assaying IGF-1R by the sandwich assay, for example, when the antibodies used in the primary reaction recognize the partial peptides at the C-terminal region of IGF-1R, the antibodies used in the secondary reaction are preferably those recognizing partial peptides other than the C-terminal region (i.e., the N-terminal region). When the antibodies used for the primary reaction recognize partial peptides at the N-terminal region of IGF-1R, the antibodies used in the secondary reaction, antibodies recognizing partial peptides other than the N-terminal region (i.e., the C-terminal region) are preferably employed.

Other types of "sandwich" assays, which can also be useful for detecting IGF-1R, are the so-called "simultaneous" and "reverse" assays. A simultaneous assay involves a single incubation step wherein the antibody bound to the solid support and labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay.

In the "reverse" assay, stepwise addition first of a solution of labeled antibody to the fluid sample followed by the addition of unlabeled antibody bound to a solid support after a suitable incubation period, is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays. In one embodiment, a combination of antibodies of the present invention specific for separate epitopes can be used to construct a sensitive three-site immunoradiometric assay.

This type of assays may also be used to quantify IGF-1R expression in whatever "sample" it may present itself. Thus, in certain aspects, the sandwich assay includes:

(i) a method for quantifying expression levels of IGF-1R in a test fluid, comprising reacting the antibody specifically reacting with a partial peptide at the N-terminal region of the IGF-1R immobilized on a carrier, a labeled form of the antibody specifically reacting with a partial peptide at the C-terminal region and the test fluid, and measuring the activity of the label; or (ii) a method for quantifying IGF-1R expression in a test fluid, comprising reacting the antibody specifically reacting with a partial peptide at the C-terminal region of the IGF-1R immobilized onto a carrier, the antibody specifically reacting with a partial peptide at the N-terminal region of a labeled form of the IGF-1R and the test fluid, and measuring the activity of the label; etc.

(2) Competitive binding assays rely on the ability of a labeled standard to compete with the test sample analyte for binding with a limited amount of antibody. The amount of IGF-1R protein in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

For quantifying the level of IGF-1R expression, one skilled in the art may combine and/or competitively react antibodies of the invention or fragments thereof, a test fluid and a labeled form of IGF-1R, measure a ratio of the labeled IGF-1R bound to the antibodies or fragments thereof b to thereby quantify the IGF-1R in the test fluid.

(3) Immunometric Assay

In the immunometric assay, an antigen in a test fluid and a solid phase antigen are competitively reacted with a given amount of a labeled form of the antibody of the present invention followed by separating the solid phase from the liquid phase; or an antigen in a test fluid and an excess amount of labeled form of the antibody of the present invention are reacted, then a solid phase antigen is added to bind an unreacted labeled form of the antibody of the present invention to the solid phase and the solid phase is then separated from the liquid phase. Thereafter, the labeled amount of any of the phases is measured to determine the antigen level in the test fluid.

Typical, and preferred, immunometric assays include "forward" assays in which the antibody bound to the solid phase is first contacted with the sample being tested to extract the IGF-1R from the sample by formation of a binary solid phase antibody-IGF-1R complex. After a suitable incubation period, the solid support is washed to remove the residue of the fluid sample, including unreacted IGF-1R, if any, and then contacted with the solution containing a known quantity of labeled antibody (which functions as a "reporter molecule"). After a second incubation period to permit the labeled antibody to complex with the IGF-1R bound to the solid support through the unlabeled antibody, the solid support is washed a second time to remove the unreacted labeled antibody. This type of forward sandwich assay can be a simple "yes/no" assay to determine whether IGF-1R is present or can be made quantitative by comparing the measure of labeled antibody with that obtained for a standard sample containing known quantities of IGF-1R. Such "two-site" or "sandwich" assays are described by Wide (Radioimmune Assay Method, Kirkham, ed., Livingstone, Edinburgh, 1970, pp. 199-206).

(4) Nephrometry

In the nephrometry, the amount of insoluble sediment, which is produced as a result of the antigen-antibody reaction in a gel or in a solution, is measured. Even when the amount of an antigen in a test fluid is small and only a small amount of the sediment is obtained, a laser nephrometry utilizing laser scattering can be suitably used.

Examples of labeling agents, which may be used in the above referenced assay methods (1) to (4) using labeling agents, include radioisotopes (e.g., 125I, 131I, 3H, 14C, 32P, 33P, 35S, etc., fluorescent substances, e.g., cyanine fluorescent dyes (e.g., Cy2, Cy3, Cy5, Cy5.5, Cy7), fluorescamine, fluorescein isothiocyanate, etc., enzymes (e.g., .beta.-galactosidase, .beta.-glucosidase, alkaline phosphatase, peroxidase, malate dehydrogenase, etc.), luminescent substances (e.g., luminol, a luminol derivative, luciferin, lucigenin, etc.), biotin, lanthanides, etc. In addition, a biotin-avidin system may be used as well for binding an antibody to a labeling agent.

In the immobilization of antigens or antibodies, physical adsorption may be used. Alternatively, chemical binding that is conventionally used for immobilization of proteins, enzymes, etc. may be used as well. Examples of the carrier include insoluble polysaccharides such as agarose, dextran, cellulose, etc.; synthetic resins such as polystyrene, polyacrylamide, silicone, etc.; or glass; and the like.

In another embodiment, the present invention assists in the diagnosis of cancers and tumors by the identification and measurement of the IGF-1R levels in body fluids, such as blood, serum, plasma, sputum and the like. If IGF-1R is normally present, and the development of the oncogenic disorder is caused by an abnormal quantity of the cell surface receptor (IGF-1R), e.g., expression relative to normal, the assay should compare IGF-1R levels in the biological sample to the range expected in normal, non-oncogenic tissue of the same cell type. Thus, a statistically significant increase in the amount of IGF-1R bearing cells or IGF-1R expression level in the subject relative to the control subject or subject's baseline, can be a factor that may lead to a diagnosis of an oncogenic disorder that is progressing or at risk for such a disorder. Likewise, the presence of high levels of IGF-1R indicative of cancers likely to metastasize can also be detected. For those cancers that express the antigen recognized by the antibodies of the invention, e.g., IGF-1R, the ability to detect the antigen provides early diagnosis, thereby affording the opportunity for early treatment. Early detection is especially important for cancers difficult to diagnose in their early stages.

Moreover, the level of antigen detected and measured in a body fluid sample such as blood provides a means for monitoring the course of therapy for the cancer or tumor, including, but not limited to, surgery, chemotherapy, radiation therapy, the therapeutic methods of the present invention, and combinations thereof. By correlating the level of the antigen in the body fluid with the severity of disease, the level of such antigen can be used to indicate successful removal of the primary tumor, cancer, and/or metastases, for example, as well as to indicate and/or monitor the effectiveness of other therapies over time. For example, a decrease in the level of the cancer or tumor-specific antigen over time indicates a reduced tumor burden in the patient. By contrast, no change, or an increase, in the level of antigen over time indicates ineffectiveness of therapy, or the continued growth of the tumor or cancer.

Detection of the antibody in the specimen can be accomplished using techniques known in the art such as immunoenzymatic techniques, e.g., immunoperoxidase staining technique, or the avidin-biotin technique, or immunofluorescence techniques (see, e.g., Ciocca et al., 1986, "Immunohistochemical Techniques Using Monoclonal Antibodies", Meth. Enzymol., 121:562 79 and Introduction to Immunology, Ed. Kimball, (2.sup.nd Ed), Macmillan Publishing Company, 1986, pp. 113 117). Those skilled in the art can determine operative and optimal assay conditions by routine experimentation.

A typical in vitro immunoassay for detecting IGF-1R comprises incubating a biological sample in the presence of a detectably labeled anti-IGF-1R antibody or antigen binding fragment of the present invention capable of selectively binding to IGF-1R, and detecting the labeled fragment or antibody which is bound in a sample. The antibody is bound to a label effective to permit detection of the cells or portions (e.g., IGF-1R or fragments thereof liberated from hyperplastic, dysplastic and/or cancerous cells) thereof upon binding of the antibody to the cells or portions thereof. The presence of any cells or portions thereof in the biological sample is detected by detection of the label.

The biological sample may be brought into contact with, and immobilized onto, a solid phase support or carrier, such as nitrocellulose, or other solid support or matrix, which is capable of immobilizing cells, cell particles, membranes, or soluble proteins. The support may then be washed with suitable buffers, followed by treatment with the detectably-labeled anti-IGF-1R antibody. The solid phase support may then be washed with buffer a second time to remove unbound antibody. The amount of bound label on the solid support may then be detected by conventional means. Accordingly, in another embodiment of the present invention, compositions are provided comprising the monoclonal antibodies, or binding fragments thereof, bound to a solid phase support, such as described herein.

By "solid phase support" or "carrier" is intended any support capable of binding peptide, antigen or antibody. Well-known supports or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material can have virtually any possible structural configuration so long as the coupled molecule is capable of binding to IGF-1R or an Anti-IGF-1R antibody. Thus, the support configuration can be spherical, as in a bead, or cylindrical, as in the inside surface of a test tube, or the external surface of a rod. Alternatively, the surface can be flat, such as a sheet, culture dish, test strip, etc. Preferred supports include polystyrene beads. Those skilled in the art will know many other suitable carriers for binding antibody, peptide or antigen, or can ascertain the same by routine experimentation.

In vitro assays in accordance with the present invention also include the use of isolated membranes from cells expressing a recombinant IGF-1R, soluble fragments comprising the ligand binding segments of IGF-1R, or fragments attached to solid phase substrates. These assays allow for the diagnostic determination of the effects of either binding segment mutations and modifications, or ligand mutations and modifications, e.g., ligand analogues.

A number of typical antibody strategies are known in the art for targeting both extracellular and intracellular molecules (e.g., complement and ADCC-mediated killing or the use of intrabodies). Because the biomarker protein of the present invention, especially the loss of function mutant LKB1 is expressed by cancer cells and not by corresponding normal cells, systemic administration of an IGF-1R inhibitor composition would be expected to exhibit excellent sensitivity without toxic, non-specific and/or non-target effects attendant non-target organs and tissues. IGF-1R specific antibodies, for example, can be useful to treat cancers systemically, either as conjugates with a toxin or therapeutic agent, or as naked antibodies capable of inhibiting cell proliferation or function (i.e., antagonistic antibodies).

Antibodies to IGF-1R expressing cells can be introduced into a patient such that the antibody binds to the cognate IGF-1R expressing cells and modulates or perturbs a function such as an interaction with a binding partner (IGF-I or IGF-II) and consequently mediates the growth inhibition and/or destruction of the cells and the tumor and/or inhibits the growth of the cells or the tumor.

Cancer immunotherapy using IGF-1R antibodies may follow the teachings generated from various approaches that have been successfully employed in the treatment of other types of cancer, including but not limited to colon cancer, breast cancer, prostate cancer, lung cancer, pancreatic cancer, cancer of the testes and bladder cancer. Some therapeutic approaches involve conjugation of a naked antibody to a toxin, such as the conjugation of $^{131}$I to anti-CD20 antibodies (e.g., RITUXAN, IDEC Pharmaceuticals Corp.), while others involve co-administration of antibodies and other therapeutic agents, such as HERCEPTIN (trastuzumab) with paclitaxel (Genentech, Inc).

Therapeutic methods of the invention contemplate the administration of single IGF-1R specific mAbs as well as combinations, or cocktails, of different mAbs. Such mAb cocktails may have certain advantages inasmuch as they contain mAbs that target different epitopes, exploit different effector mechanisms or combine directly cytotoxic mAbs with mAbs that rely on immune effector functionality. Such mAbs in combination may exhibit synergistic therapeutic effects. In addition, the administration of IGF-1R specific mAbs to cells identified as sensitive to treatment with an IGF-1R targeted therapy according to methods of the invention may be combined with other therapeutic agents, including but not limited to various chemotherapeutic agents. The IGF-1R specific mAbs to such "sensitive" patients may be administered in their "naked" or unconjugated form, or may have therapeutic agents conjugated to them.

Antibody formulations targeting IGF-1R expressing cells previously identified according to methods of the invention as being sensitive to treatment with an IGF-1R targeted therapy may be administered via any route capable of delivering the therapeutic antibodies e.g., IGF-1R specific mAbs to the tumor site. Potentially effective routes of administration include, but are not limited to, intravenous, intraperitoneal, intramuscular, intratumor, intradermal, and the like. Treatment will generally involve the repeated administration of the antibody preparation via an acceptable route of administration such as intravenous injection (IV), typically at a dose in the range of about 0.1 to about 10 mg/kg body weight. Doses in the range of 10-500 mg mAb per week may be effective and well tolerated. "therapeutic antibodies" refers to any IGF-1R inhibitor, preferably the humanized IGF-1R specific mAb disclosed herein and also described in U.S. Pat. No. 7,244, 444. Therapeutically effective "dosages" of the therapeutic antibodies may be determined using well known methods.

In vivo, the effect of a therapeutic composition comprising as a main ingredient the therapeutic antibodies may be evaluated in a suitable animal model. For example, xenogenic cancer models wherein human cancer explants or passaged xenograft tissues are introduced into immune compromised animals, such as nude or SCID mice, are appropriate in relation to cancer and have been described (Klein. et al. (1997) Nature Medicine 3:402-408). For example, WO 98/16628 describes various xenograft models of human prostate cancer capable of recapitulating the development of primary tumors, micrometastasis, and the formation of osteoblastic metastases characteristic of late stage disease. Efficacy may be predicted using assays that measure inhibition of tumor formation, tumor regression or metastasis, and the like.

The present invention comprises embodiments wherein any of the biomarkers, wild type LKB1 or the loss of function mutant LKB1 are underexpressed or overexpressed to any degree relative to a control. In an embodiment of the invention, a cell (e.g., in a tumor) that underexpresses a gene encoding wild type LKB1 by an amount at least about 1.5 fold less than that of a control cell is considered IGF-1R sensitive.

Underexpression of the biomarker protein, e.g., LKB1 in a cell is relative to that of an IGF-1R resistant cell includes any cell whose growth of survival is not significantly reduced by exposure to a given IGF-1R inhibitor. Methods of growing such resistant cells are known to one skilled in the art.

In an embodiment of the invention, a cell is sensitive or responsive to an IGF-1R inhibitor if its growth or survival or ability to metastasize is reduced to any detectable degree. In an embodiment of the invention, a cell is sensitive if the $IC_{50}$ for an inhibitor is less than 1000 nM (e.g., 750 nM, 500 nM, 100 nM, 50 nM, 25 nM, 1 nM, 2 nM, or 3 nM or less).

The present invention includes methods comprising the use of any IGF-1R inhibitor known in the art.

Other Chemotherapeutic Agents

The present invention further embodies methods wherein a IGF-1 R inhibitor is administered to a subject in association with a therapeutic procedure (e.g., surgical tumorectomy or anti-cancer radiation therapy) and/or a further chemotherapeutic agent, such as any anti-cancer chemotherapeutic agent. Representative chemotherapeutic inhibitors include tyrosine kinase inhibitors-Erlotinib, Herceptin, VEGH inhibitors-AVASTIN, mTOR inhibitors such as the one described in U.S. Pat. No. 7,091,213 and AKT inhibitors. Exemplary AKT inhibitors are disclosed in various patent applications, including, but not limited to one of US2008/280899, US2006/270673, US2007/082906, US2007/043001, US2006/205765, US2008/009507, US2008!161317, US2005/288294, US2008/015212, US2008/255143, US2008/287457, US2009/062327, US2005/222155, US2005/130977, US2005/159422, US2004/116433, US2004/116432, US2007/254901, US2004/143117, US2004/122012, the contents of each of which is incorporated by reference herein in its entirety.

The cancer need not, in all cases, be determined, in the methods of the present invention, as absolutely IGF-1R inhibitor sensitive or resistant. For example, in one embodiment of the invention, a colorectal tumor's cells assessed for LKB1 expression levels might be determined to be only moderately IGF-1R inhibitor sensitive or moderately IGF-1R inhibitor resistant but not completely FTI resistant. This judgment can be reached, for example, by comparing the level of LKB1 expression to that of other cancer cell lines. Thus, based on the assessment of a cancer's relative sensitivity or resistance to an IGF-1R targeted therapy, a clinician or doctor of ordinary skill in the art may make a reasoned decision, based on, e.g., the particular needs of the patient involved, other regimens the patient is receiving, and the exigencies of the particular situation as to whether to undertake a treatment regimen with a IGF-1R inhibitor or a combination thereof.

If a tumor is identified using the criteria set forth herein to comprise IGF-1R sensitive cells, the patient with the cells can be identified as a candidate for IGF-1R therapy, selected and treated accordingly.

Anti-cancer therapeutic procedure includes tumor irradiation. Tumor irradiation may comprises one of X-ray radiation, UV-radiation, 7-radiation, microwave radiation, and combinations thereof. The methods of to invention further comprise administering to a patient in need thereof the humanized antibody—IGF-1R inhibitor in combination with an anti-emetic agent, wherein the agent is selected from the group consisting of ondansetron hydrochloride, granisetron hydrochloride, metroclopramide, domperidone, haloperidol, cyclizine, lorazepam, prochlorperazine, dexamethasone, levomepromazine, and tropisetron.

For general information concerning formulations, see, e.g., Gilman, et al., (eds.) (1990), The Pharmacological Bases of Therapeutics, 8th Ed., Pergamon Press; A. Gennaro (ed.), Remington's Pharmaceutical Sciences, 18th Edition, (1990), Mack Publishing Co., Easton, Pa.; Avis, et al., (eds.) (1993) Pharmaceutical Dosage Forms: Parenteral Medications Dekker, New York; Lieberman, et al., (eds.) (1990) Pharmaceutical Dosage Forms: Tablets Dekker, New York; and Lieberman, et al., (eds.) (1990), Pharmaceutical Dosage Forms: Disperse Systems Dekker, New York, Kenneth A. Walters (ed.) (2002) Dermatological and Transdermal Formulations (Drugs and the Pharmaceutical Sciences), Vol 119, Marcel Dekker. See also U.S. Pat. No. 6,632,455; and European patent no. 1039908.

Inert, pharmaceutically acceptable carriers used for preparing pharmaceutical compositions of IGF-1R inhibitors described herein can be solid or liquid. Solid preparations include powders, tablets, dispersible granules, capsules, cachets and suppositories. The powders and tablets may, in an embodiment of the invention, comprise from about 5 to about 70% active ingredient. Solid carriers are known in the art, e.g., magnesium carbonate, magnesium stearate, talc, sugar, and/or lactose. Tablets, powders, cachets and capsules can. In an embodiment of the invention, be used as solid dosage forms suitable for oral administration.

Equivalents

Those skilled in the art will recognize, or be able to ascertain using no more than routine experimentation, many equivalents to the specific embodiments of the invention described herein. Such equivalents are intended to be encompassed by the following claims.

EXAMPLE 1

Crosstalk between the epithelial growth factor receptor (EGFR) and insulin like growth factor receptor (IGF-1R) has been well documented. The small-molecule EGFR tyrosine kinase inhibitors (TKI), including gefitinib and erlotinib, are currently used in the treatment of late stage lung cancer. Pre-clinical studies appear to suggest that response to EGFR inhibitors can be substantially increased by combining with an IGF-1R inhibitors such as MK-0646. IGF-1R is over-expressed in several cancers including breast, colon and lung. Several studies in multiple tumor types have suggested that IGF-1R levels can be predictive of response to anti-IGF-1R therapy (Cao L et al., Cancer Res 2008; Zha J et al., Mol Cancer Ther 2009).

Figure 1B:
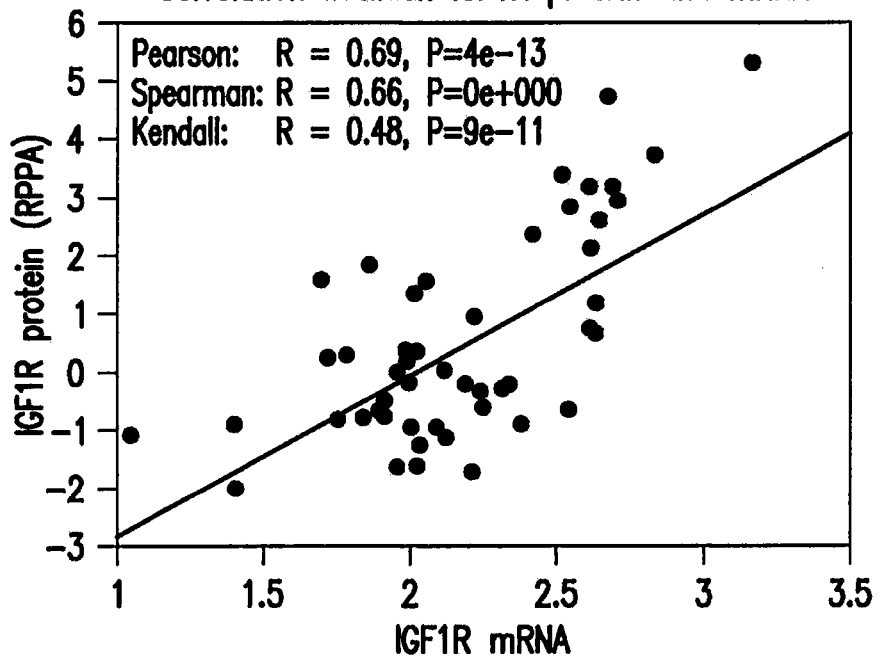
Figure 2A:
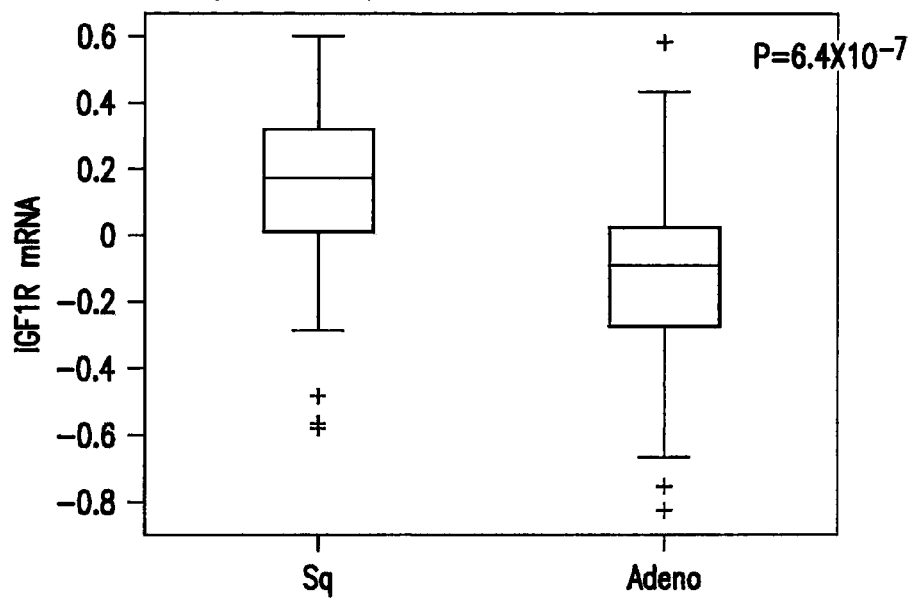
FIG. 2: Diversity in the expression of IGF-1R in human NSCLC. A) Comparison of IGF-1R mRNA expression NSCLC classified based on histopathological characteristics of the tumor; Adenocarcinoma (Ad; n=59), Squamous cell carcinoma (Sq; n=54). B) Correlation between IGF-1R mRNA expression and IGF-1R protein levels as measured by immuno-histochemistry (IHC) by staining with anti-IGF-1R antibody (G11 clone; Ventana). The staining intensity and number of cells positive for IGF-1R were determined and scored (H-score). A correlation between IGF-1R expression levels as measured by mRNA and IHC was observed (n=88). C) Relative distribution of IGF-1R expression in a set of human NSCLC samples (n=100) were plotted. Diversity in IGF-1R staining was observed. D) NSCLC samples were classified based on into Adenocarcinoma (Adeno) or Squamous cell carcinoma (Sq) and relative distribution of IGF-1R staining intensity were plotted.
Figure 2B:
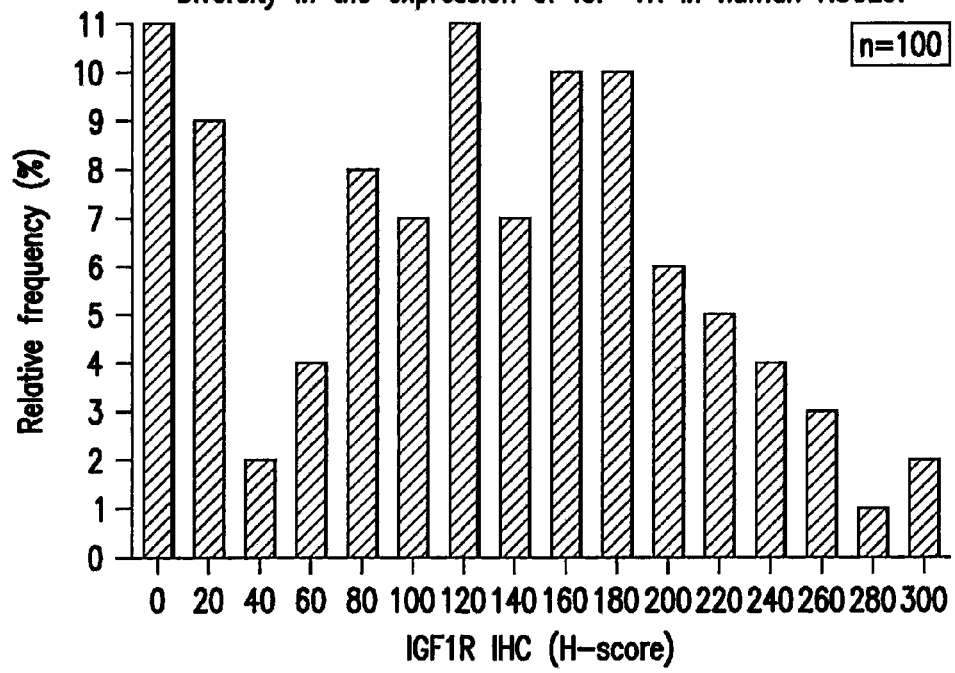
Figure 2C:
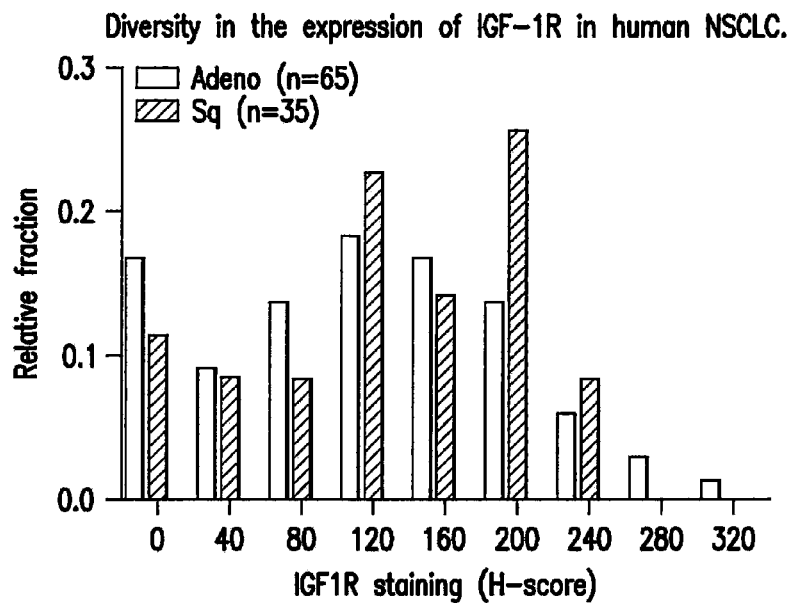
Figure 2D:
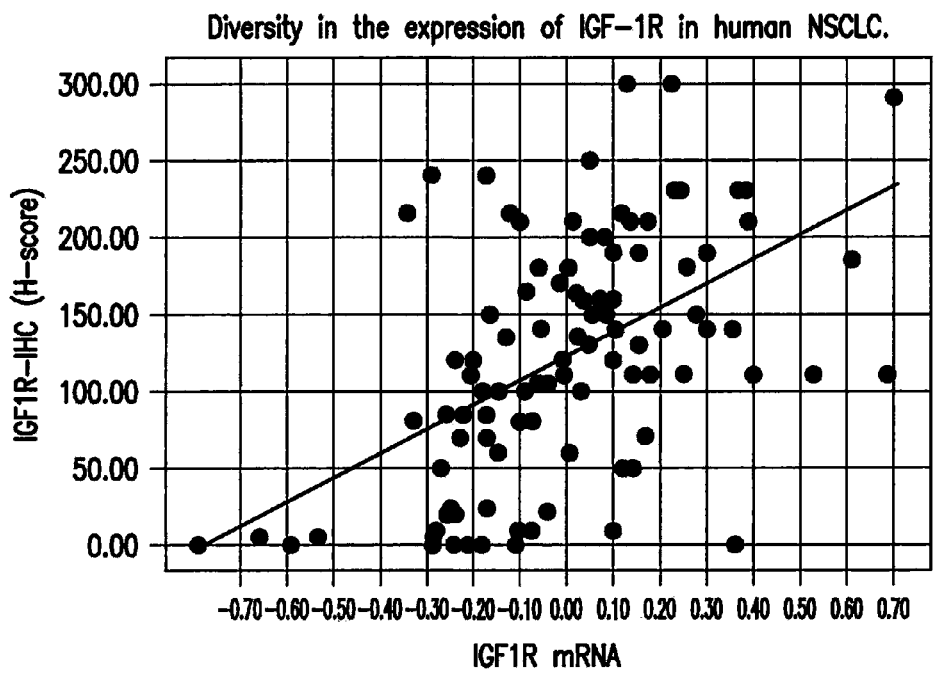

To identify biomarkers associated with sensitivity to MK-0646 or MK-0646/erlotinib combination, the inventors assessed anchorage independent growth inhibition in a set of NSCLC cell lines (N=26). Diversity in response to either MK-0646 or erlotinib or the combination was observed in this panel. NSCLC cell lines expressing high levels of IGF-1R were more sensitive to MK-0646 as a single agent and to MK-0646/erlotinib combination (FIG. 1A, B). Xenograft sensitivity assessments with NSCLC cell lines expressing high levels of IGF-1R (NCI-H2122, A549, NCI-H460) showed significant sensitivity to MK-0646 as compared to erlotinib. Likewise, MK-0646/erlotinib combination showed significant combination benefit in 2/3 models. In contrast, xenograft models with low levels of IGF-1R expression (SK-MES & NCI-H520) did not show sensitivity to MK-0646. Note that in the A549 model despite high levels of IGF-1R expression no significant combination benefit with erlotinib/MK-0646 combination was observed. These results suggested that IGF-1R levels may be used as a patient selection biomarker for the clinical development of MK-0646 & erlotinib combination in NSCLC. A strong correlation between the expression levels of IGF-1R mRNA and IGF-1R total protein was also observed in the panel of NSCLC cell lines (FIG. 1C). Taken together, either IGF-1R mRNA or IGF-1R protein may be used as a predictive biomarker for MK-0646/erlotinib response.

Evaluating of IGF-1R Expression in Human Lung Cancer Specimen:

To investigate the prevalence of IGF-1R over-expression in human NSCLC, IGF-1R mRNA levels were determined using micro-array analysis. IGF-1R expression levels were compared between Squamous cell carcinoma and Adenocarcinoma of NSCLC. Consistent with previous studies, IGF-1R expression was significantly elevated (1.9 fold) in squamous cell carcinoma as compared to Adenocarcinoma. In order to test IGF-1R expression in clinical lung cancer samples an immuno-histochemistry (IHC) assay was developed in collaboration with Ventana Medical Inc. Utilizing this IHC assay IGF-1R expression levels were analyzed in a set of NSCLC tumors obtained from the Moffitt tumor collection. Diversity in IGF-1R expression was observed in this set of NSCLC specimens. About 31% of the NSCLC tumors had high levels of IGF-1R expression (>180 H-score). While 37% of the squamous cell carcinoma had high levels of IGF-1R expression, a smaller percentage (27%) of adenocarcinoma showed high IGF-1R expression. Note that the mRNA based analysis showed a more dramatic over-expression of IGF-1R in squamous cell carcinoma. The difference between mRNA and IHC analysis could be due to low representation of Squamous cell carcinoma in the IHC analysis or due to differential post-transcriptional processing of IGF-1R. IGF-1R expression at the level of mRNA and protein as estimated by IGF-1R-IHC were compared between matched FFPE sections and FF tumors from the same patients. A significant correlation ($P=2.14 \times 10^{-8}$) between IGF-1R mRNA and IHC staining for membrane IGF-1R expression was observed. A similar correlation between IGF-1R mRNA and protein expression as measured by reverse-phase protein arrays was also observed. These results show a prevalence of IGF-1R over expression in squamous cell carcinoma and suggest an enrichment of responders to MK-0646 in this subset of NSCLC patients.

Figure 3A:
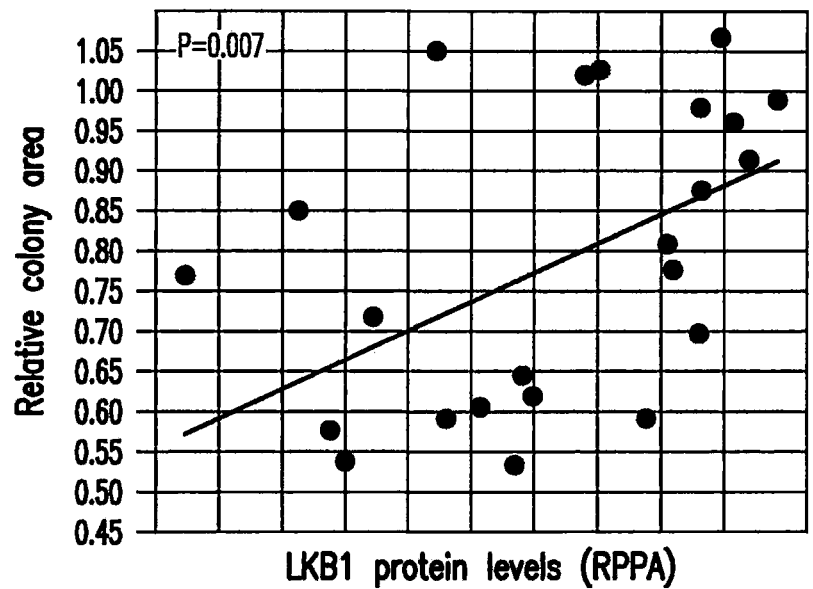
FIG. 3: Correlation of LKB1 protein levels with response to MK-0646 in a panel of NSCLC cell lines. A) Anchorage independent growth in the presence of MK-0646 in soft agar was potted against LKB1 protein levels as determined by RPPA. A significant association between LKB1 protein levels and sensitivity to MK-0646 was identified by Spearman correlation. B) Correlation between LKB1 protein levels by western blot analysis with MK-0646 sensitivity. Cell lines with very low levels of LKB1 (below the detection limit of western blot analysis) were classified as LKB1-low cell lines. C) Correlation between IGF-1R and LKB1 protein levels by RPPA with sensitivity to MK-0646. MK-0646 sensitive cell lines (Green) are enriched in IGF-1R high, LKB1 low quadrant.
Figure 3B:
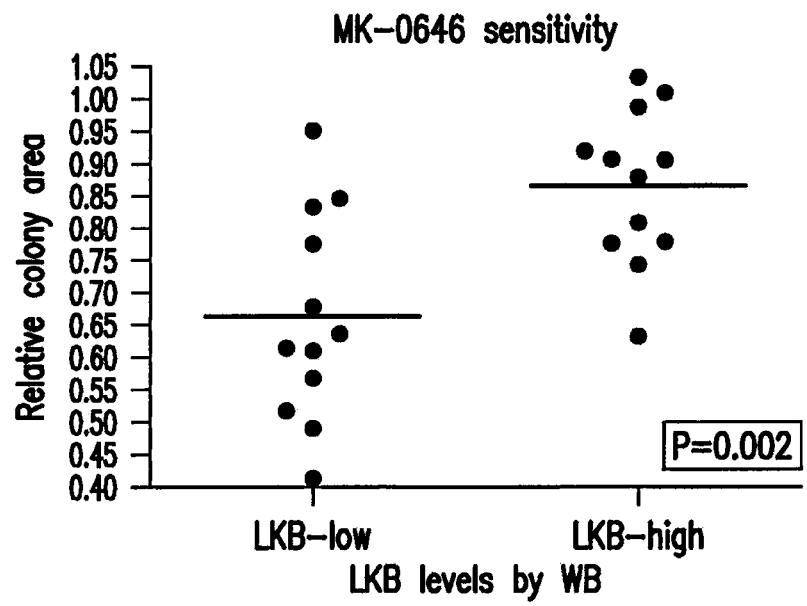
Figure 3C:
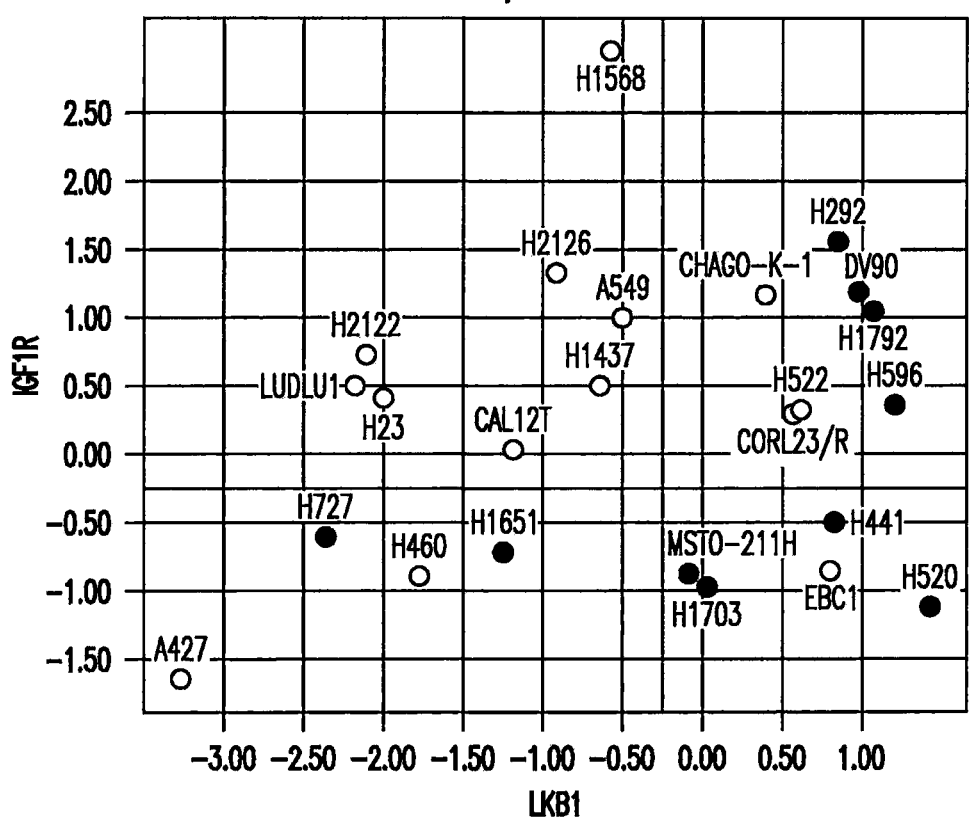

LKB1 as a Biomarker:

That IGF-1R levels were predictive of response to MK-0646 as a single agent or in combination with erlotinib are detailed above. Here the inventors show that the loss of a tumor suppressor gene, LKB1 is associated with sensitivity to MK-0646. Loss of function mutations in LKB1 has been previously associated with lung cancer progression. A correlation between sensitivity to MK-0646 and LKB1 protein levels were identified using reverse-phase protein arrays (RPPA; FIG. 3A). LKB1 protein levels were further verified by western blot analysis (FIG. 3B). LKB1 protein was not detectable (LKB1-low; n=11) in a sub-set of cell lines, while LKB1 proteins were high in other cell lines. MK-0646 sensitivity was significantly enriched in the "LKB1-low" cell lines. Strikingly, sensitivity to MK-0646 as a single agent (FIG. 3C) or in combination with erlotinib (data not shown) was enriched in the IGF-1R high cell lines expressing low levels of LKB1. In Colo699 cell line LKB1 protein expression was comparable to other "LKB1-high" cell lines. However, this cell line was very sensitive to MK-0646. This is likely due to autocrine activation by IGF-1 over-expression in this cell line.

Figure 4A:
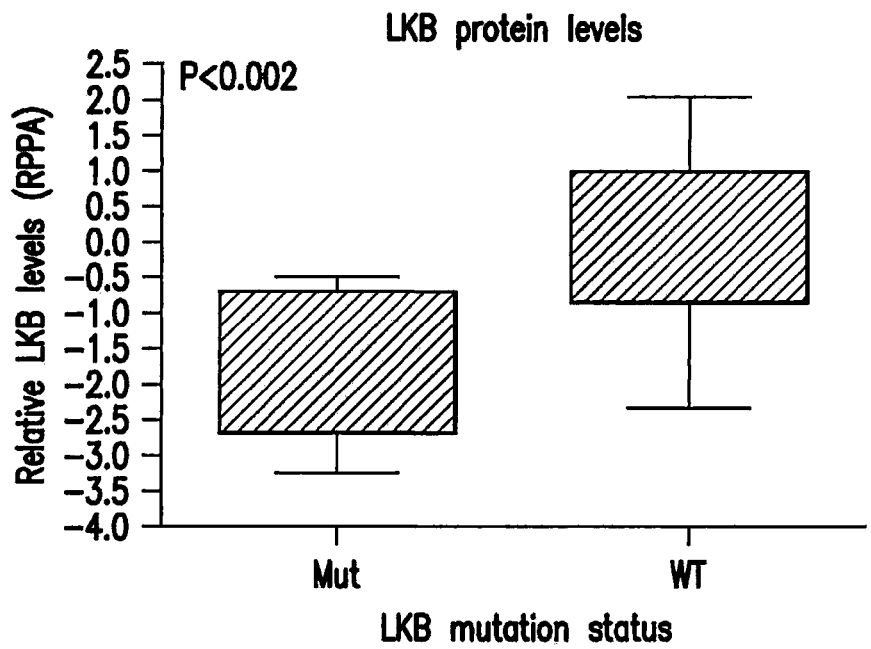
FIG. 4: Correlation of LKB1/STK11 mutation with LKB1 protein levels and sensitivity to MK-0646. LKB1 mutational status was determined by sequencing of LKB1 gene as described in cancer genome database (COSMIC; Sanger Institute). A) Correlation between LKB1 protein levels as determined by RPPA analysis and LKB1 mutational status. LKB1 protein levels were compared between the LKB1/STK11 mutants and wild type cell line using unpaired t-test. A significant reduction in LKB1 protein was observed in LKB1/STK11 mutants. B) Correlation between MK-0646 sensitivity and LKB1/STK11 mutation. Sensitivity to MK-0646 treatment as measured by anchorage independent growth was correlated with mutational status of LKB1/STK11 gene. Unpaired t-test identified a statistically significant sensitivity to MK-0646 in LKB1/STK11 mutants NSCLC cell lines.
Figure 4B:
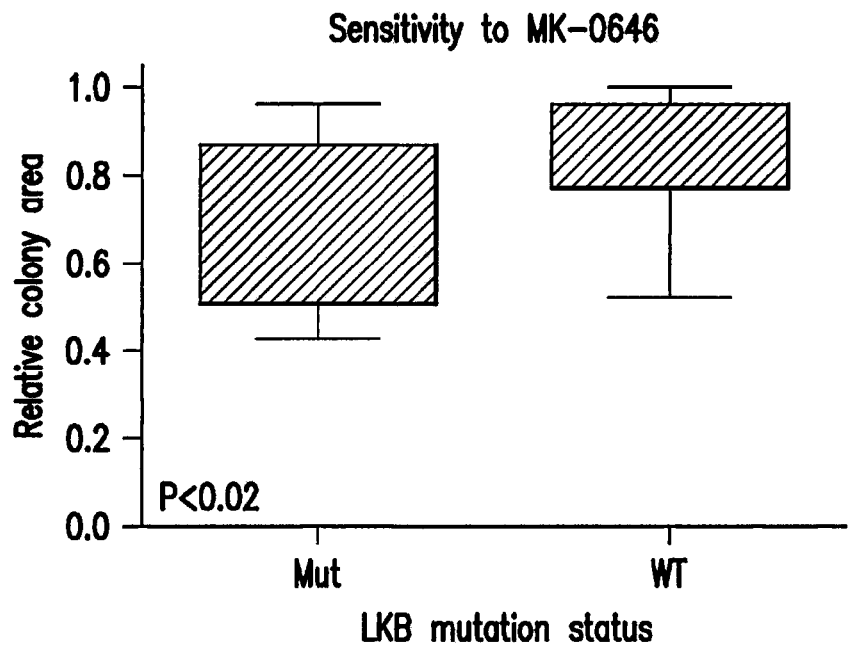

LKB1/STK 1 Loss of Function Mutation and Sensitivity to MK-0646:

Herein, the inventors correlated LKB1 protein levels and sensitivity to MK-0646 with loss of function mutations in LKB1/STK11 gene. The mutational status in the coding region of LKB1/STK11 gene was available in cell lines (n=15) in the panel from cancer genome project (COSMIC database, Sanger Institute). The nature of the loss of function mutation included non-sense or frame shift mutations or small deletions in the coding region of LKB1 gene (Table 1). LKB1 protein levels were significantly reduced (FIG. 4A) in NSCLC cell lines harboring loss of function mutation in LKB1/STK11 gene. Also a significant sensitivity to MK-0646 was observed in LKB1/STK11 mutant NSCLC cell lines (FIG. 4B). These data suggest that loss of function mutation in LKB1/STK11 may sensitize patients to anti-IGF-1R therapy.

TABLE 1

| NSCLC cell line | AA Mutation in STK11/LKB1 | CDS Mutation in STK11/LKB1 | Zygosity | Nature of substitution |
|---|---|---|---|---|
| H23 | p.W332* | c.996G > A | Homozygous | p.W332* (Substitution-Nonsense) |
| H2122 | p.P281fs*6 | c.842delC | Homozygous | p.P281fs*6 (Deletion-Frameshift) |
| A549 | p.Q37* | c.109C > T | Homozygous | p.Q37* (Substitution-Nonsense) |
| H2126 | p.? | c.? ?del? | Homozygous | Deletion? |
| A427 | p.? | c.1 734del734 | Homozygous | Deletion |
| H460 | p.Q37* | c.109C > T | Homozygous | p.Q37* (Substitution-Nonsense) |

Methods:
Cell Lines and Culture Conditions:

All NSCLC cell lines were obtained from ATCC and maintained in 10% fetal bovine serum, FBS (Hyclone) containing media (DMEM or RPMI; Invitrogen Inc) supplemented with pen-strep (Invitrogen) at 37° C. according to the instructions from ATCC.

Anchorage Independent Growth Assay

Soft agar assays were conducted in 96 well glass bottom plates (MATRICAL). Cells were seeded at a concentration of 3,000-9,000 cells per WELL in 100 µl RPMI 1640 (INVITROGEN) supplemented with 14% FBS and 0.3% (w/v) SEQ-PLAQUE Agarose (Lonza Rockland, Inc) on top of a bottom layer of consisting of the same culture media supplemented with 0.8% agarose. Compounds were added in 100µl of culture media supplemented after agarose had solidified. Cells were incubated for 7-14 days before staining overnight with LAVA CELL(Active Motif). Colonies were quantified using an ISOCYTE laser scanning cytometer. The ability of MK-0646 to inhibit anchorage independent growth alone or in combination with standard of care agents was evaluated in a soft agar colony forming assay.

Xenograft Growth Assessment:

Human NSCLC cells ($2.5 \times 10^6$) were injected subcutaneously into the right flank of 4-6 week old nu/nu mice (Charles River Laboratories). When tumors reached a size of ~300 mm3 (Length*Width*Width*0.5), mice were randomized into treatment groups. Mice (n=8/group) were dosed with vehicle once per week for 3 weeks (qwkx3) (20 mM L-Histidine, 150 mM NaCl, 0.5% PS80 pH=6) or 2 mpk of MK-0646 intra-peritoneal mg/kg MK-0646 (qwk) or Erlotinib (50 mg/kg by oral gavage) daily or in combination with MK-0646 for 3-4 weeks as indicated. Animals were weighed and tumor volumes were determined by calipering 2 times per week during the study and at termination. Tumor weight was determined at termination. On day 21 or 28 Animals were sacrificed by $CO_2$ asphyxiation. Mice were sacrificed 24 hr after the final dose. At time of sacrifice, the tissue samples were collected and processed.

Reverse Phase Protein Array Analysis:

Serial 2-fold dilutions of protein lysates (dPER buffer, Thermo Scientific) from NSCLC cells grown in the presence of 10% FBS were printed in duplicate on 150 nitrocellulose backed glass slides. The dilution series of each lysate insure that each antigen-antibody combination is analyzed in its linear dynamic range. For this study the slides were probed with various total of phosphor-specific antibodies. Overall 58 unique antibodies encompassing the LKB1, NFκB, PI3K, mTOR, and receptor tyrosine kinases were assayed. Each pathway was probed with a battery of phosphorylation specific antibodies to encompass the interconnectivity of cellular pathways (Table 1).

Reverse Phase Protein Microarrays were manufactured as described below. Briefly, 20 nl of denatured protein lysates (10 mM Tris, 100 mM NaCl, 1 mM EDTA, 20 mM Na4P2O7, 1% TRITON-X-100, 10% glycerol, 0.1% SDS, 0.5% deoxycholate, 2 mM Na3VO4, 1 mM PMSF) were immobilized onto nitrocellulose coated glass slides using an Auchon 2407microarrayer. Arrays were blocked for 2 hours at room temperature with Casein containing 0.1% TWEEN-20, which was followed by blocking of endogenous biotin, incubation with primary antibody at a concentration of 1:1000, and biotinylated secondary antibody at 1:5000. Arrays were developed with 3,3'diaminobenzidine terahydrochloride (DAB) chromogen.

RPPA Normalization and Correlation Analyses.

Technical and biological replicates for each antibody and cell line were produced to assess the reproducibility of RPPA readings. Technical replicates consisted of arrays printed in duplicate and probed with the same antibody using the protocol described above. Biological replicates were cell lysates derived from the same cell line grown in different wells. Normalization is critical to account for differences in intensity ranges for each protein readout and differences in total protein content of cell lines (Hennessy et. al., Stemke-Hale et. al.). First, median z-scores were used to standardize readings from each antibody array, then cell lines were normalized using a second z-score across arrays. It is necessary to normalize a second time to make cell line readings comparable as there may be differences in protein loading as a result of sample processing.

Technical and biological replicates were combined so that each cell line maps to a single RPPA profile. The following normalization steps were taken:

1) standardize each antibody array using median z-score
2) combine technical replicate z-score readings by taking the mean z-score
3) standardize each cell line profile using median z-score
4) combine biological replicate z-scores by taking the mean z-score Western Blot Analysis For western blot analysis total protein lysates from cells (~0.3 million) cultured in 6 well plates were harvested in SDS gel loading dye (INVITROGEN). Samples were western blotted with indicated total or phosphospecific antibodies followed by a secondary antibody (Cell Signaling Technology, CST) and then incubated with SUPERSIGNAL chemiluminescence substrate (Pierce). The blots were then exposed to a Kodak BIOMAX Light Film. LKB1 (27D10) Rabbit mAb CST #3050 The antibodies against ERK, P-ERK (Thr202/Tyr204), AKT and p-AKT (Ser473), IGF-IR S6K & P-S6K (T389), IRS1 & P-IRSI (8302) and actin were obtained from CST.

Immuno Histochemical Analysis of IGF-1R in Human Tumor Samples:

The IGF-lR IHC analyses were carried out using Ventana's Benchmark staining platform on pafaffin embedded sections (FFPE) of the tumor tissue. The anti-IGF-lR primary antibody was obtained from Ventana Medical Systems, Inc. (Catalog No. 790-4346; immunogen sequence: ENKLPEPEELDLEPENM (SEQ ID NO: 16)). Antigen recovery was conducted under "Standard" conditions with CC1 buffer (VMSI, Catalog No. 950-124). Slides were incubated with the appropriate dilution (1/160) of the stock concentration of the primary antibody for 16 minutes at 37° C. Stock antibody concentration refers to the concentration at which the antibody is sold commercially concentrations of commercial antibodies are not always made available by manufacturers. As a negative control, specimens were incubated with rabbit immunoglobulin under the same conditions. The anti-Insulin-like Growth Factor Receptor Type I antibody was detected using the ultraView™ detection kit (VMSI, Catalog No. 760-500). Enzymatic detection of anti-Insulin-like Growth Factor Receptor Type I antibody was accomplished with a horseradish peroxidase conjugate (HRP), followed by reaction with hydrogen peroxide in the presence of diaminobenzidine (DAB) and copper sulfate. The secondary antibody, conjugate, and all chromogen reagents were applied at the default times.

Staining intensity was measured on a semi-quantitative scale of 0 (or negative) to 3. The percentage of cells staining positively at each intensity level was recorded. The scores were based on localization of InsulinIGF1R to the membrane and cytoplasm. Excessive background staining and/or lack of contrast, if present, were also noted. H scores were calculated (McCarty et al. 1986). An H score, which combines the components of staining intensity and the percentage of positive cells, is defined as:

[1*(percentage of cells staining at 1)]+[2*(percentage of cells staining at 2)]+[3*(percentage of cells staining at 3)]

H Score.

---

What is claimed is:

1. A method for treating a dalotuzumab responsive cancer, in a patient, comprising: (a) determining the expression level of liver kinase B1 (LKB1), in a cancer cell from the patient, and when said expression is determined to be lower than that of a control cell; (b) administering, to said patient, a therapeutically effective amount of dalotuzumab.

2. The method of claim 1 wherein the expression level of liver kinase B1 (LKB1) is determined by measuring the expression level of LKB1 mRNA.

3. The method of claim 1 wherein the expression level of liver kinase B1 (LKB1) is determined by measuring the expression level of LKB1 protein in said cell.

4. The method of claim 1, further comprising administering, to the patient, a therapeutic agent selected from the group consisting an Akt inhibitor, a tyrosine kinase inhibitor, a VEGF (vascular epidermal growth factor) inhibitor and an mTOR (mammalian target of rapamycin) inhibitor.

5. The method of claim 1 wherein the cancer is selected from the group consisting of lung cancer, lung adenocarcinoma, non small cell lung cancer, pancreatic cancer, exocrine pancreatic carcinoma, colon cancer, colorectal carcinoma, colon adenocarcinoma, colon adenoma, bladder carcinoma, sarcoma, breast cancer, ovarian cancer and prostate cancer.

6. The method of claim 1, further comprising administering to said patient an anti-cancer therapeutic procedure, wherein said therapeutic procedure is tumor irradiation.

7. The method of claim 6, wherein said tumor irradiation is selected from the group consisting of X-ray radiation, UV-radiation, γ-radiation, microwave radiation, and combinations thereof.

8. The method of claim 1, further comprising administering to said patient an anti-emetic agent which is selected from the group consisting of ondansetron hydrochloride, granisetron hydrochloride, metroclopramide, domperidone, haloperidol, cyclizine, lorazepam, prochlorperazine, dexamethasone, levomepromazine, and tropisetron.

9. A method for assessing that dalotuzumab inhibits growth or survival of a neoplastic cell comprising obtaining the cell from a patient, and determining that said cell underexpresses liver kinase B1 (LKB1) relative to said expression in a control cell; wherein the inhibitor is determined to inhibit said growth or survival when said underexpression is observed; and administering a therapeutically effective amount of the dalotuzumab to said patient.

10. A method for selecting a patient with a cancerous condition for treatment with dalotuzumab comprising determining that a cancerous cell from said patient underexpresses liver kinase B1 (LKB1) relative to expression of LKB1 in a control cell; wherein the patient is selected when LKB1 expression is determined to be underexpressed in the cancerous cell; and administering a therapeutically effective amount of the dalotuzumab to said selected patient.

11. A method for selecting an insulin-like growth factor-1 receptor (IGF-1R) inhibitor therapy to treat a cancerous condition in a patient comprising determining that a cancerous cell taken from said patient underexpresses liver kinase B1 (LKB1) relative to expression of LKB1 in a control cell; wherein dalotuzumab is selected for the therapy when said LKB1 underexpression is observed; and administering a therapeutically effective amount of the dalotuzumab to said patient.

12. A method for diagnosing whether a patient has a cancerous condition that will respond to therapy with dalotuzumab comprising determining that a cancerous cell taken from said patient underexpresses liver kinase B1 (LKB1) relative to a control cell, diagnosing the patient with the condition when the underexpression is determined; and administering a therapeutically effective amount of dalotuzumab to said diagnosed patient.

* * * * *